United States Patent [19]

Schickaneder et al.

[11] Patent Number: 4,757,080
[45] Date of Patent: Jul. 12, 1988

[54] 1,4-DIHYDROPYRIDINE DERIVATIVES

[75] Inventors: Helmut Schickaneder, Eckental; Peter Mörsdorf, Langenzenn; Armin Buschauer; Walter Schunack, both of Berlin; Heidrun Engler, Cadolzburg; Hartmut Vergin; Kurt H. Ahrens, both of Nürnberg, all of Fed. Rep. of Germany

[73] Assignee: Heumann Pharma GmbH & Co., Nuremberg, Fed. Rep. of Germany

[21] Appl. No.: 51,300

[22] Filed: May 19, 1987

[30] Foreign Application Priority Data

Jun. 24, 1986 [DE] Fed. Rep. of Germany ....... 3621104

[51] Int. Cl.$^4$ .................. A61K 31/44; C07D 401/12
[52] U.S. Cl. .................................. 514/338; 514/341; 546/271; 546/278
[58] Field of Search ................ 546/271, 278; 514/338, 514/341

[56] References Cited

FOREIGN PATENT DOCUMENTS 0041359 12/1981 European Pat. Off. .
0106462 4/1984 European Pat. Off. .
0119050 9/1984 European Pat. Off. .
2211454 10/1972 Fed. Rep. of Germany .
2407115 10/1974 Fed. Rep. of Germany .

0226876 11/1985 Japan .................. 546/278

Primary Examiner—Jane T. Fan
Attorney, Agent, or Firm—Burns, Doane, Swecker & Mathis

[57] ABSTRACT

New compounds which act on the cardiac circulation and correspond to the general formula

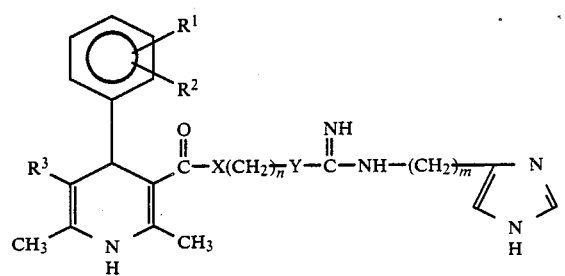

and may be used for the treatment of cardiac diseases, in certain forms of hypertension and in diseases of arterial occlusion are described.

Methods of preparation for these compounds and medicaments containing these compounds are also described.

6 Claims, No Drawings

1,4-DIHYDROPYRIDINE DERIVATIVES

This invention relates to new compounds which act on the cardiac circulation and in particular 1,4-dihydropyridines which manifest calcium antagonistic and/or $H_2$-receptor agonistic activities and are therefore eminently suitable for use in cardiac diseases, certain forms of hypertension and diseases of arterial occlusion.

1,4-Dihydropyridine calcium antagonists such as, for example, nifedipine, are known therapeutic agents which, for example, inhibit the flow of calcium into the cell.

Thus nifedipine(1,4-dihydro-2,6-dimethyl-4-(2-nitrophenyl)-3,5-pyridine carboxylic acid dimethyl ester) which is a known compound of the 1,4-dihydropyridine series lowers the arterial resistance and has a very marked coronary dilatory effect without inhibiting the activity of the heart in therapeutic doses.

Calcium antagonists have, however, inter alia a direct negative chronotropic and negative inotropic action on the heart, which has the disadvantage that it may give rise to tachycardia when used in therapy.

It would therefore be preferable to treat cardiac diseases with an active substance which in addition has a direct positive inotropic action.

It is therefore an object of the present invention to provide new active substances which combine within a single molecule a calcium antagonistic and an $H_2$-agonistic action as well as having an advantageous clinically relevant overall activity.

This problem is solved by the present invention.

This invention thus relates to 1,4-dihydropyridine derivatives corresponding to the general formula I

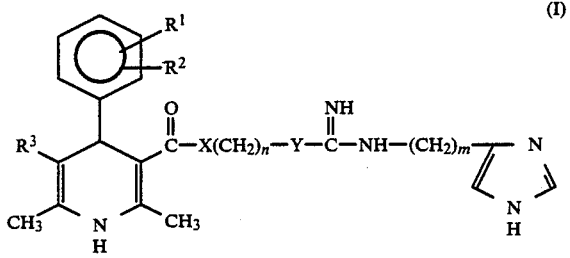

(I)

wherein $R^1$ and $R^2$ denote, independently of one another, a hydrogen atom, a straight chained or branched, optionally substituted $C_1$–$C_4$-alkyl group, a halogen atom, a nitro group or a trifluoromethyl group or together they stand for a 1,2,5-oxadiazole group; $R^3$ denotes a nitro group or the group

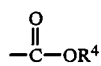
$$-\overset{\overset{O}{\|}}{C}-OR^4$$

wherein $R^4$ stands for a straight chained or branched, optionally substituted $C_1$–$C_4$-alkyl group; X denotes an oxygen atom or the group NH; Y denotes the group NH or a bond; n represents an integer with a value from 1 to 16 and m has the value 2 or 3; and to the physiologically acceptable salts thereof.

In the general formula I, $R^1$ and $R^2$ denote, independently of one another, a hydrogen atom or a straight chained or branched $C_1$–$C_4$-alkyl group. Examples of such $C_1$–$C_4$-alkyl groups include the methyl, ethyl, n-propyl, i-propyl, n-butyl, i-butyl, sec.-butyl and tert.-butyl group, the methyl group and ethyl group being preferred. The methyl group is particularly preferred. Further, $R^1$ and $R^2$ may stand for a halogen atom, e.g. a chlorine, bromine or iodine atom, a nitro group or a trifluoromethyl group. $R^1$ and $R^2$ preferably stand for a halogen atom, most preferably a chlorine atom. The nitro group is also preferred. The substituents $R^1$ and $R^2$ are preferably attached in the 2- and/or 3-position of the phenyl ring. The $C_1$–$C_4$-alkyl group may be substituted or unsubstituted. If the group is substituted, the substituent is preferably a halogen atom, in particular a chlorine atom, a $C_1$–$C_4$-alkoxy group, e.g. a methoxy, ethoxy, i-propoxy, n-propoxy, n-butoxy or i-butoxy or sec.-butoxy or tert.-butoxy group or an aryl group, in particular a phenyl group, monosubstitution being preferred. The groups $R^1$ and $R^2$ may also together denote a 1,2,5-oxadiazole group which is attached by its carbon atoms 3 and 4 to the phenyl group, preferably at the 2 and 3 positions of the phenyl group, by condensation.

$R^3$ denotes a nitro group or the group $$-\overset{\overset{O}{\|}}{C}-OR^4,$$

in which $R^4$ stands for a straight chained or branched $C_1$–$C_4$-alkyl group as defined above. This $C_1$–$C_4$-alkyl group may be unsubstituted or carry one or more substituents; it is preferably mono-substituted. The substituents may be halogen atoms as defined above, preferably chlorine atoms, or they may be $C_1$–$C_4$-alkoxy groups, as defined above.

X denotes an oxygen atom or the group NH and Y denotes the group NH or a single bond; n represents an integer with a value from 1 to 16, preferably from 2 to 6, and m has the value 2 or 3, preferably 3.

A preferred group of compounds according to the invention is characterised in that $R^1$ and $R^2$ denote, independently of one another, a hydrogen atom, a straight chained or branched $C_1$–$C_4$-alkyl group optionally substituted by a halogen atom, by a $C_1$–$C_4$-alkoxy group or by an aryl group, in particular a phenyl group; or they may denote a halogen atom, a nitro group or a trifluoromethyl group, and the substituents $R^1$ and $R^2$ are attached in the 2- and/or 3-position of the phenyl ring; or $R^1$ and $R^2$ may together represent a 1,2,5-oxadiazole group which is attached by condensation at its 3- and 4-positions to the 2- and 3-positions of the phenyl group; $R^3$ denotes a nitro group or the group $$-\overset{\overset{O}{\|}}{C}-OR^4$$

wherein $R^4$ represents a straight chained or branched $C_1$–$C_4$-alkyl group which may be substituted by one or more halogen atoms or by one or more $C_1$–$C_4$-alkoxy groups; X denotes an oxygen atom or the group NH; Y denotes the group NH or a bond; n represents an integer with a value from 1 to 16 and m has the value 3.

Another preferred group of compounds according to the invention is characterised in that $R^1$ and $R^2$ denote, independently of one another, a hydrogen atom, a chlorine atom or a nitro group and the substituents $R^1$ and $R^2$ are attached to the 2- and/or 3-position of the phenyl ring; $R^3$ denotes the group

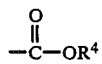

wherein R[4] denotes a straight chained or branched $C_1$-$C_4$-alkyl group optionally substituted by one or more halogen atoms or by one or more $C_1$-$C_4$-alkoxy groups; X denotes an oxygen atom or the group NH; Y denotes the group NH or a bond; n denotes an integer with a value from 2 to 6 and m has the value 3.

Lastly, another group of compounds according to the invention is characterised in that R[1] denotes a hydrogen atom, R[2] denotes a nitro group attached to the 2- or 3-position of the phenyl ring, R[3] denotes the group

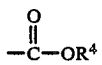

wherein R[4] is a straight chained or branched $C_1$-$C_4$-alkyl group optionally substituted by one or more halogen atoms or by one or more $C_1$-$C_4$-alkoxy groups; X denotes an oxygen atom, Y denotes the groups NH, n represents an integer with a value from 1 to 16 and m has the value 3.

The compounds according to the invention may be converted into their physiologically acceptable salts by means of suitable acids. These salts may be obtained in known manner by reaction with, for example, mineral acids such as hydrochloric, hydrobromic or hydriodic acid, phosphoric acid, nitric acid or sulphuric acid or by reaction with organic acids such as formic acid, acetic acid, propionic acid, tartaric acid, citric acid, fumaric acid, methanesulphonic acid, embonic acid, etc. The present invention therefore also covers all physiologically acceptable salts of the above-described compounds corresponding to the general formula I.

The invention also extends to all stereoisomeric and all tautomeric forms and hydrates of the above-described compounds corresponding to the general formula I.

The compounds according to the invention may be prepared as follows:

(a) Compounds corresponding to the general formula I in which R[1], R[2], R[3], X, m and n have the meanings defined above and Y stands for NH may be prepared (a1) by the reaction of an isothiuronium salt corresponding to the general formula II

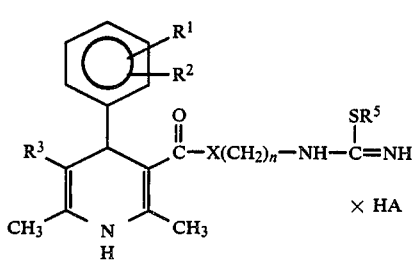

wherein R[1], R[2], R[3], X and n have the meanings indicated in the definition of the general formula I, R[5] denotes an optionally substituted alkyl group and A denotes a halogen atom or the group $OSO_2OR^5$ with a m-(1H-imidazol-4-yl)-alkylamine corresponding to the formula III

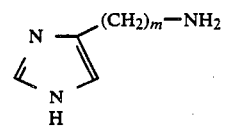

wherein m has the value 2 or 3.

In the general formula II, R[5] denotes an optionally substituted alkyl group, preferably an optionally substituted $C_1$-$C_4$-alkyl group as defined above in connection with the general formula I. The alkyl group denoted by R[5] may be substituted or unsubstituted. If it is substituted, then the substituent may be a phenyl or a benzyl group, preferably a benzyl group.

The symbol A denotes a halogen atom as defined above in connection with the general formula I, preferably an iodine atom, or the group $OSO_2OR^5$ in which R[5] has the meaning already indicated.

The components are preferably reacted together in equimolar quantities and in a solvent at temperatures within the range of room temperature and the boiling point of the solvent. The solvents used are preferably pyridine, acetonitrile or alcohols, in particular n-butanol.

(a2) by the reaction of an amine corresponding to the general formula IV

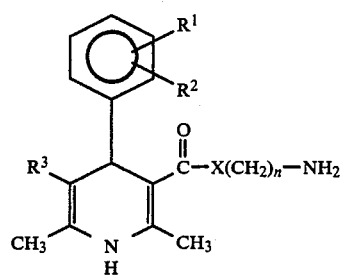

wherein R[1], R[2], R[3], X and n have the meaning already indicated in connection with the general formula I with a compound corresponding to the general formula V

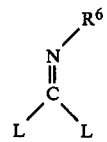

wherein R[6] denotes a cyano group or a benzoyl group and L denotes a replaceable group such as —SR[7] or —OR[7] in which R[7] denotes an alkyl group, preferably as $C_1$-$C_4$-alkyl group as defined in connection with the general formula I or an aryl group, preferably a phenyl group, to produce an intermediate compound corresponding to the general formula VI

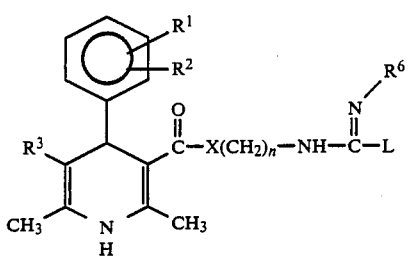 (VI)

and reaction of this intermediate compound VI with a m-(1H-imidazol-4-yl)-alkylamine corresponding to the formula III

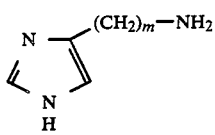 (III)

wherein m has the value 2 or 3, to produce a compound corresponding to the general formula VII

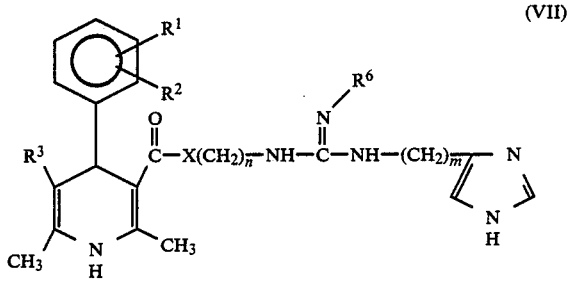 (VII)

which is subsequently converted to a compound corresponding to the general formula I by acid catalysed hydrolysis.

In the first stage of this process, the reactants corresponding to formulae IV and V are preferably used in equimolar quantities. The usual inert organic solvents may be used for this stage of the process. Chlorinated hydrocarbons such as dichloromethane or chloroform, ethers such as tetrahydrofuran or dioxane, acetonitrile, acetone, pyridine and dimethylformamide are preferred. The reaction temperatures are generally in the range of from 0° C. to the boiling point of the solvent used.

In the second stage of this process the reactants VI and III are also preferably used in equimolar quantities, and the same solvents and temperatures are employed as in the first stage of the process.

The third stage of this process, i.e. hydrolysis of the intermediate compound VII to form the end product corresponding to the general formula I, is carried out in dilute inorganic acids, dilute organic acids or mixtures of the two at reflux temperatures. The following acids are preferred: Hydrochloric acid, hydrobromic acid, hydriodic acid, sulphuric acid, phosphoric acid, acetic acid and mixtures of the inorganic acids mentioned and acetic acid; or (a3) by the reaction of an amine corresponding to the general formula IV

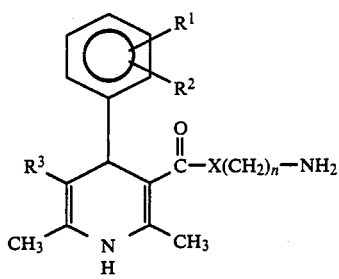 (IV)

wherein $R^1$, $R^2$, $R^3$, X and n have the meanings indicated with reference to the general formula I with a compound corresponding to the general formula VIII

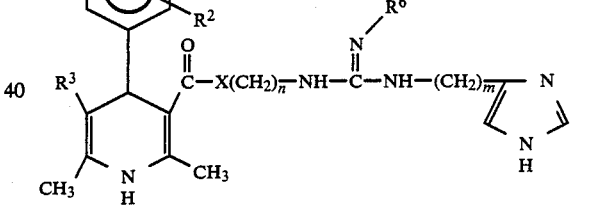 (VIII)

wherein $R^6$ and L have the meanings indicated in connection with the general formula V and m has the value 2 or 3 to produce a compound corresponding to the general formula VII

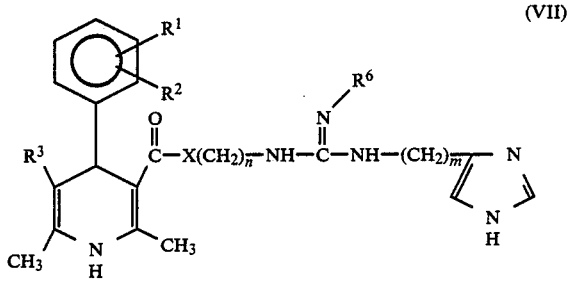 (VII)

which is then hydrolysed to produce a compound corresponding to the general formula I. Hydrolysis is carried out as described in connection with variation (a2) of the process; or (a4) by the reaction of an amine corresponding to the general formula IV

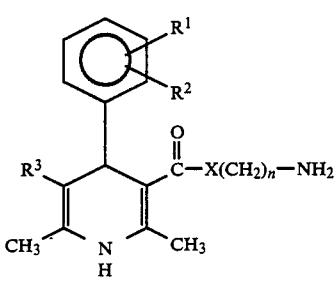 (IV)

wherein $R^1$, $R^2$, $R^3$, X and n have the meanings already indicated with reference to the general formula I, with a compound corresponding to the general formula IX

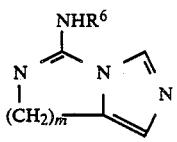

wherein R⁶ has the meaning indicated with reference to the general formula V and m has the value 2 or 3, to produce an intermediate compound corresponding to the general formula VII

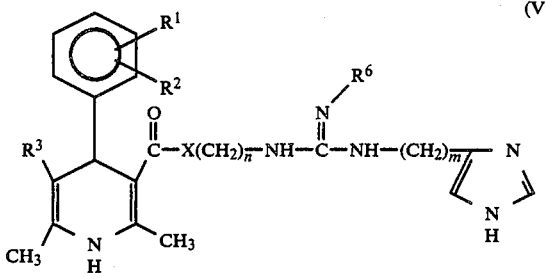

followed by hydrolysis of the resulting intermediate compound VII to a compound corresponding to the general formula I.

This variation of the process is carried out under the same conditions as those described in connection with variations (a2) and (a3) of the process.

(b) Compounds corresponding to the general formula I in which $R^1$, $R^2$, $R^3$, X, m and n have the meanings indicated with reference to the general formula I and Y denotes a single bond are prepared by the reaction of an imidoester corresponding to the general formula X

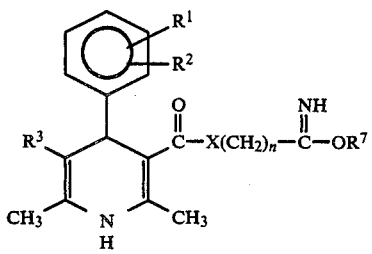

wherein $R^1$, $R^2$, $R^3$, X and n have the meanings indicated with reference to the general formula I and $R^7$ denotes a $C_1$–$C_4$-alkyl group as defined with reference to the general formula I with a m-(1H-imidazol-4-yl)-alkylamine corresponding to formula III

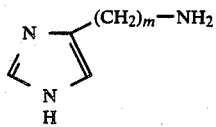

wherein m has the value 2 or 3.

The reaction is carried out in a suitable solvent and at temperatures which may range from room temperature to the boiling point of the solvent used, the reflux temperature being preferred.

Any of the usual inert organic solvents may be used, alcohols being preferred, in particular those corresponding to the group $R^7$.

The molar ratio of the reactants III and X may vary from 3:1 to 1:1 and is preferably within the range of from 1:1 to 1.2:1.

The compounds obtained by variations (a1) to (b) of the process are isolated and purified by the usual methods, for example by chromatographic methods, recrystallisation, extraction, etc.

The amines corresponding to the general formula IV used as starting materials are known compounds and may be prepared by known methods (see DE-OS No. 2 117 571, DE-OS No. 3 420 784 and EP-OS No. 0 151 006).

The isothiuronium salts corresponding to the general formula II are obtained by methods known in the literature, for example by acylation of the amines corresponding to the general formula IV with benzoyl isothiocyanate, alkaline hydrolysis of the benzoyl group and alkylation of the resulting thiourea with known alkylating agents such as alkyl halides or sulphates, etc.

The compounds according to the invention may be made up into any desired formulations for administration. The present invention therefore also relates to medicaments containing at least one compound according to the invention for use in human or veterinary medicine. Medicaments of this kind are conventionally prepared with the addition of one or more pharmaceutical carriers or diluents.

The compounds according to the invention may therefore be made up into preparations for oral, buccal, topical, parenteral or rectal administration. For oral administration, for example, the medicament may be provided in the form of tablets, capsules, powders, solutions, syrups or suspensions prepared with the aid of acceptable diluents by the usual methods. For buccal administration, the medicament may be prepared in the form of tablets or sachets made up according to the usual formulations.

The compounds according to the invention may also be formulated for parenteral administration by bolus injection or for continuous infusion. Formulations for injection may be prepared in single dose ampoules or in multiple dose containers with added preservatives.

The medicaments may take the form of suspensions, solutions or emulsions in oily or aqueous carriers and they may contain formulating auxiliaries such as suspension or dispersing agents and/or stabilizers.

Alternatively, the active ingredient may be prepared in powder form to be reconstituted with a suitable carrier such as sterile, pyrogen-free water before use.

The compounds according to the invention may also be formulated for rectal administration, for example in the form of retention enemas or suppositories containing the usual suppository excipients such as cocoa butter or other glycerides.

For topical application, the compounds according to the invention may be formulated in the usual manner as ointments, creams, gels, lotions, powders or sprays.

A suitable daily dose of the compounds according to the invention for oral administration is made up of 1 to 4 doses with a total of 5 mg of 1 g/day, according to the patient's condition. One unit dose of the medicament according to the invention contains from 0.1 mg to 30 mg of active ingredient, preferably from 1 mg to 20 mg.

It may in individual cases be necessary to deviate from the quantities indicated, depending on the individual response to the active ingredient, the nature of the formulation and the time or the time interval at which the medicament is administered. Thus, for example, less than the minimum quantity indicated above may be sufficient in certain cases whereas in other cases it may be necessary to exceed the given upper limit.

The compounds according to the invention are distinguished by a novel pharmacological overall activity which has not hitherto been known or described. The new class of structures according to this invention has both a calcium antagonistic component and an $H_2$-agonistic component.

The calcium antagonistic activity of the compounds according to the invention was determined on isolated guineapig's ileum which had been stimulated with barium chloride (slightly modified method of A. Fleckenstein et al, *Arzneim.-Forsch.* 29, 230–246 (1971)).

The $H_2$ agonistic activity ($pD_2$-values) is determined by the method of J. M. van Rossum, (1963), Cumulative dose-response Curves, II. Technique for the making of dose-response curves in isolated organs and the evaluation of drug parameters, *Arch. Intern. Pharmacodyn. Therap.* 143, 299–307.

Pharmacological Data

|  | $pA_2$-value ($BaCl_2$) | $pD_2$-value |
|---|---|---|
| Compound of Example 1 | 7.42 | 7.32 |
| Compound of Example 7 | 6.96 | 7.41 |
| Compound of Example 8 | 7.52 | 6.48 |
| Nifedipine (comparison) | 8.02 | — |
| Impromidine (comparison) | — | 7.67 |

EXAMPLES OF PREPARATION

Example 1

$N^1$-[2-[1,4-Dihydro-2,6-dimethyl-3-methoxycarbonyl-4-(2-nitrophenyl)-pyridine-5-carboxy]ethyl]-$N^2$-[3-(1H-imidazol-4-yl)propyl]-guanidine-hydriodide

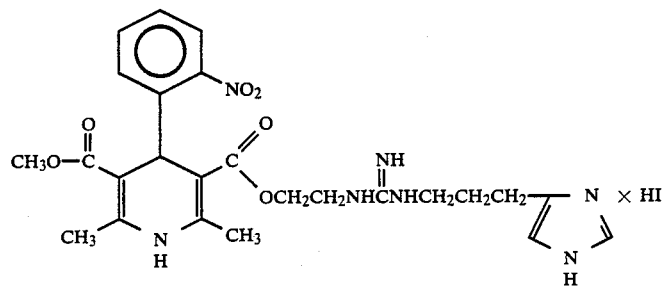

(a) 1,4-Dihydro-2,6-dimethyl-3-methoxycarbonyl-4-(2-nitrophenyl)-5-(2-phthalimido-ethoxy)carbonyl-pyridine

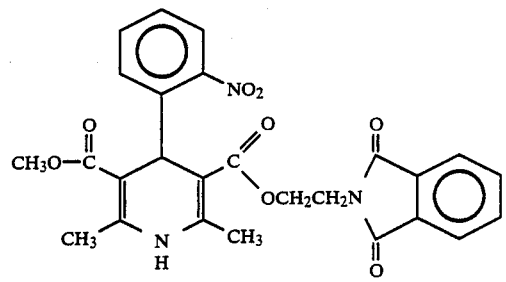

14.95 g (60 mmol) of the methyl ester of 2-(2-nitrobenzylidene)-acetic acid and 16.46 g (60 mmol) of 3-aminocrotonic acid-(2-phthalimidoethyl)ester are boiled in 150 ml of ethanol for 16 hours. When the reaction mixture has cooled to room temperature, the precipitate formed is suction filtered, washed with a small quantity of cold ethanol and recrystallised from ethanol.

21.53 g (71%) of yellow crystals melting at 229°–230° C. are obtained.

$C_{26}H_{23}N_3O_8$ (505.48). Rf ($CH_2Cl_2/CH_3OH$ 95:5): 0.35.

(b) 1,4-Dihydro-2,6-dimethyl-3-methoxycarbonyl-4-(2-nitrophenyl)-5-(2-amino-ethoxy)carbonyl-pyridine

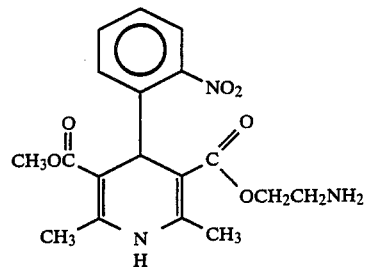

1.5 ml (30 mmol) of hydrazine hydrate in 7.5 ml of ethanol are added dropwise to a boiling solution of 5.05 g (10 mmol) of 1,4-dihydro-2,6-dimethyl-3-methoxycarbonyl-4-(2-nitrophenyl)-5-(2-phthalimidoethoxy)carbonylpyridine in 50 ml of ethanol. Boiling is continued for 2 hours and the reaction mixture is then cooled and concentrated by evaporation under vacuum. The residue is stirred up with 25 ml of 2N-hydrochloric acid for 30 minutes at room temperature and the precipitated solid is removed by suction filtration and the filtrate is adjusted to pH 10 with conc. ammonia. The product is extracted three times with 30 ml portions of methylene chloride and the organic phases obtained are then dried and concentrated by evaporation. 2.91 g (77%) of a yellow amorphous solid is obtained as residue which is used without further purification.

$C_{18}H_{21}N_3O_6$ (375.38). Rf ($CH_2Cl_2/CH_3OH$ 90:10): 0.3.

(c)
$N^1$-Benzoyl-$N^2$-[2-[1,4-dihydro-2,6-dimethyl-3-methoxycarbonyl-4-(2-nitropheny)-pyridine-5-carboxy]ethyl]-thiourea

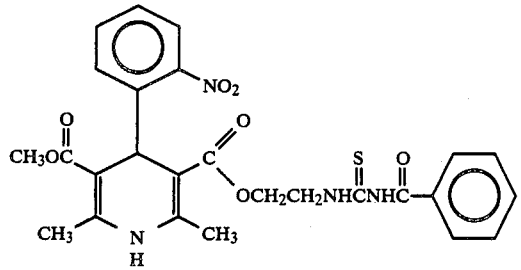

1.50 g (4 mmol) of 1,4-Dihydro-2,6-dimethyl-3-methoxycarbonyl-4-(2-nitrophenyl)-5-(2-aminoethoxy)-carbonylpyridine and 0.65 g (4 mmol) of benzoyl isothiocyanate are boiled in 15 ml of dichloromethane for 2 hours. After removal of the solvent by evaporation under vacuum, the residue is crystallized with tert.-butyl-methyl ether. 2.0 g (93%) of a yellow solid melting at 96°–98° C. are obtained.

$C_{26}H_{26}N_4O_7S$ (538.58). Rf ($CH_2Cl_2/CH_3OH$ 95:5): 0.57.

(d)
S-Methyl-N-[2-[1,4-dihydro-2,6-dimethyl-3-methoxycarbonyl-4-(2-nitrophenyl)-pyridine-5-carboxy]-ethyl]-isothiuronium iodide

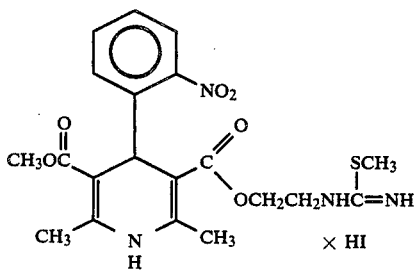

2.00 g (3.7 mmol) of $N^1$-Benzoyl-$N^2$-[2-[1,4-dihydro-2,6-dimethyl-3-methoxycarbonyl-4-(2-nitrophenyl)-pyridine-5-carboxy]-ethyl]-thiourea and 0.51 g (3.7 mmol) of potassium carbonate are boiled in 50 ml of methanol and 15 ml of water for 20 minutes. The mixture is diluted with 100 ml of water and extracted with 4×50 ml of dichloromethane. After dehydration over sodium sulphate, the organic phases are filtered and concentrated by evaporation under vacuum. The residue is taken up with 40 ml of ethanol. 0.23 ml (3.7 mmol) of methyl iodide are added. After 20 hours at room temperature, the solution is concentrated by evaporation under vacuum and the residue is triturated with tert.-butyl methyl ether. 1.35 g (63%) of yellow crystals melting at 96°–98° C. are obtained.

$C_{20}H_{25}IN_4O_6S$ (576.41). Rf ($CH_2Cl_2/CH_3OH$ 90:10): 0.4.

(e)
$N^1$-[2-[1,4-dihydro-2,6-dimethyl-3-methoxycarbonyl-4-(2-nitrophenyl)-pyridine-5-carboxy]-ethyl]-$N^2$-[3-(1H-imidazol-4-yl)propyl]-guanidine hydriodide 1.00 g (1.73 mmol) of S-Methyl-N-[2-[1,4-dihydro-2,6-dimethyl-3-methoxycarbonyl-4-(2-nitrophenyl)-pyridine-5-carboxy]ethyl]-isothiuronium iodide and 0.22 g (1.73 mmol) of 3-(1H-imidazol-4-yl)-propylamine are boiled in 15 ml of acetonitrile for 3 hours. After removal of the solvent by evaporation under vacuum, the crude product is chromatographically purified on silica gel with ethyl acetate/ethanol (80:20) as solvent. The main fraction yields 0.82 g (72%) of a yellow, amorphous solid after evaporation under vacuum.

$C_{25}H_{32}IN_7O_6$ (653.47). Rf ($CH_3COOC_2H_5/CH_3OH/NH_4Cl/NH_3$ buffer 50:47.5:2.5): 0.66.

| $^1$H—NMR data ($CD_3OD$, TMS as internal standard) | $\delta =$ | 1.8–2.2 | (m) | 2H |
|---|---|---|---|---|
| | | 2.3 | (s) | 3H |
| | | 2.4 | (s) | 3H |
| | | 2.6–2.9 | (t) | 2H |
| | | 3.1–4.6 | (m) | 6H |
| | | 3.6 | (s) | 3H |
| | | 5.1 | (broad) | 6H replaceable by $D_2O$ |
| | | 5.85 | (s) | 1H |
| | | 7.1 | (s) | 1H |
| | | 7.3–8.1 | (m) | 5H ppm |

Example 2

$N^1$-[3-[1,4-Dihydro-2,6-dimethyl-3-methoxycarbonyl-4-(2-nitrophenyl)-pyridine-5-carboxy]-propyl]-$N^2$-[3-(1H-imidazol-4-yl)propyl]-guanidine hydriodide

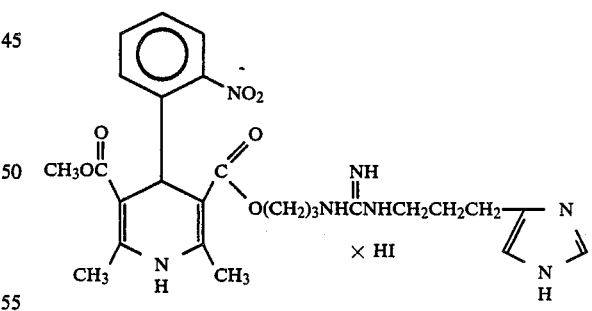

(a)
1,4-Dihydro-2,6-dimethyl-3-methoxycarbonyl-4-(2-nitrophenyl)-5-(3-phthalimido-propoxy)carbonyl-pyridine 12.2 g (47%) of yellow crystals melting at 174°–175° C. are obtained by a method analogous to that of Example 1(a) from 12.5 g (50 mmol) of 2-(2-nitrobenzylidene)-acetoacetic acid methyl ester and 14.4 g (50 mmol) of 3-aminocrotonic acid-(3-phthalimidopropyl)ester.

$C_{27}H_{25}N_3O_8$ (519.51). Rf ($CH_2Cl_2/CH_3OH$ 95:5): 0.6.

(b)
1,4-Dihydro-2,6-dimethyl-3-methoxycarbonyl-4-(2-nitrophenyl)-5-(3-aminopropoxy)-carbonyl-pyridine By the method of Example 1(b) from 12.0 g (23 mmol) of 1,4-dihydro-2,6-dimethyl-3-methoxycarbonyl-4-(2-nitrophenyl)-5-(3-phthalimidopropoxy)-carbonyl-pyridine and 4.2 ml (69 mmol) of hydrazine hydrate in ethanol.

The crude product is purified on silica gel with dichloromethane/methanol (80:20) as solvent. The yellow main fraction yields 6.93 g (77%) of a brownish yellow, viscous oil after concentration by evaporation under vacuum.

$C_{19}H_{23}N_3O_6$ (389.41). Rf ($CH_2Cl_2/CH_3OH$ 80:20): 0.2.

(c)
$N^1$-Benzoyl-$N^2$-[3-[1,4-dihydro-2,6-dimethyl-3-methoxycarbonyl-4-(2-nitrophenyl)-pyridine-5-carboxy]-propyl]-thiourea 7.6 g (77%) of a dark yellow oil obtained from 6.93 g (17.8 mmol) of 1,4-dihydro-2,6-dimethyl-3-methoxycarbonyl-4-(2-nitrophenyl)-5-(3-aminopropoxy)carbonyl-pyridine and 2.90 g (17.8 mmol) of benzoyl isothiocyanate by the method analogous to that of Example 1(c).

$C_{27}H_{28}N_4O_7S$ (552.60). Rf ($CH_2Cl_2/CH_3OH$ 95:5): 0.5.

(d)
S-Methyl-N-[3-[1,4-dihydro-2,6-dimethyl-3-methoxycarbonyl-4-(2-nitrophenyl)-pyridine-5-carboxy]-propyl]-isothiuronium iodide Prepared by a method analogous to that of Example 1(d) from 7.6 g (14 mmol) of $N^1$-benzoyl-$N^2$-[3-[1,4-dihydro-2,6-dimethyl-3-methoxycarbonyl-4-(2-nitrophenyl)pyridine-5-carboxy]propyl]-thiourea. 6.1 g (75%) of a yellow, amorphous foam.

$C_{21}H_{27}IN_4O_6S$ (590.24). Rf ($CH_2Cl_2/CH_3OH$ 90:10): 0.4.

$N^1$-[3-[1,4-Dihydro-2,6-dimethyl-3-methoxycarbonyl-4-(2-nitrophenyl)-pyridine-5-carboxy]propyl]-$N^2$-[3-(1H-imidazol-4-yl)propyl]-guanidine hydriodide Obtained by a method analogous to that of Example 1(e) from 1.00 g (1.69 mmol) of S-methyl-N-[3-[1,4-dihydro-2,6-dimethyl-3-methoxycarbonyl-4-(2-nitrophenyl)-pyridine-5-carboxy]-propyl]-isothiuronium iodide and 0.21 g (1.69 mmol) of 3-(1H-imidazol-4-yl)propylamine in acetonitrile. 0.80 g (71%) of a yellow, amorphous solid is obtained after chromatographic purification of the crude product on silica gel with ethyl acetate/methanol (80:20) as solvent.

$C_{26}H_{34}IN_7O_6$ (667.50). Rf ($CH_3COOC_2H_5/CH_3OH/NH_4Cl/NH_3$ buffer 50:47.5:2.5): 0.5.

| $^1$H—NMR data (CD$_3$OD, TMS as internal standard) | δ = | 1.7–2.1 | (m) | 4H | |
|---|---|---|---|---|---|
| | | 2.3 | (s) | 3H | |
| | | 2.35 | (s) | 3H | |
| | | 2.7 | (t) | 2H | |
| | | 3.0–3.4 | (m) | 4H | |
| | | 3.6 | (s) | 3H | |
| | | 3.9–4.4 | (m) | 2H | |
| | | 4.9 | (broad) | 6H replaceable by D$_2$O | |
| | | 5.8 | (s) | 1H | |
| | | 6.95 | (s) | 1H | |
| | | 7.3–7.9 | (m) | 5H ppm. | |

Example 3
$N^1$-[2-[1,4-Dihydro-2,6-dimethyl-3-methoxycarbonyl-4-(3-nitrophenyl)-pyridine-5-carboxy]ethyl]-$N^2$-[3-(1H-imidazol-4-yl)propyl]-guanidine hydriodide

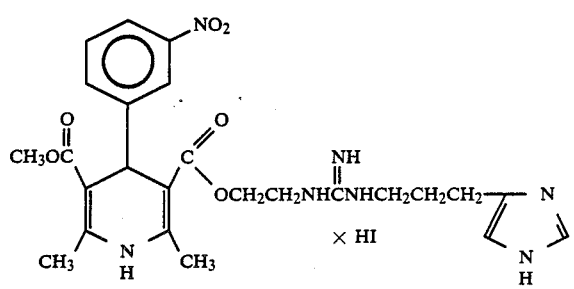

(a)
1,4-Dihydro-2,6-dimethyl-3-methoxycarbonyl-4-(3-nitrophenyl)-5-(2-phthalimidoethoxy)carbonyl-pyridine Prepared by a method analogous to that of Example 1(a) from 14.95 g (60 mmol) of 2-(3-nitrobenzylidene)-acetoacetic acid methyl ester and 16.46 g (60 mmol) of 3-amino-crotonic acid-(2-phthalimidoethyl)ester in ethanol. 25.25 g (83%) of yellow crystals melting at 181°–182° C. are obtained.

$C_{26}H_{23}N_3O_8$ (505.48). Rf ($CH_2Cl_2/CH_3OH$ 95:5): 0.5.

(b)
1,4-Dihydro-2,6-dimethyl-3-methoxycarbonyl-4-(3-nitrophenyl)-5-(2-aminoethoxy)-carbonyl-pyridine 13.48 g (93%) of a yellow solid are obtained by a method analogous to that of Example 1(b) from 20.22 g (40 mmol) of 1,4-dihydro-2,6-dimethyl-3-methoxycarbonyl-4-(3-nitrophenyl)-5-(2-phthalimidoethoxy)carbonyl pyridine and 5.8 ml (120 mmol) of hydrazine hydrate.

$C_{18}H_{21}N_3O_6$ (375.38). Rf ($CH_2Cl_2/CH_3OH$ 90:10): 0.33.

(c)
$N^1$-Benzoyl-$N^2$-[2-[1,4-dihydro-2,6-dimethyl-3-methoxycarbonyl-4-(3-nitrophenyl)-pyridine-5-carboxy]ethyl]-thiourea Prepared by a method analogous to that of Example 1(c) from 11.26 g (30 mmol) of 1,4-dihydro-2,6-dimethyl-3-methoxycarbonyl-4-(3-nitrophenyl)-5-(2-aminoethoxy) carbonyl-pyridine and 4.89 g (30 mmol) of benzoyl isothio cyanate. 7.41 g (46%) of a yellow, amorphous solid are obtained after chromatographic purification on silica gel with dichloromethane/methanol (97:3) as solvent.

$C_{26}H_{26}N_4O_7S$ (538.38). Rf ($CH_2Cl_2/CH_3OH$ 90:10): 0.6.

(d)
S-Methyl-N-[2-[1,4-dihydro-2,6-dimethyl-3-methoxycarbonyl-4-(3-nitrophenyl)-pyridine-5-carboxy]ethyl]-isothiuronium iodide 1.09 g (27%) of a yellowish, amorphous solid obtained by a method analogous to that of Example 1(d)

from 3.80 g (7 mmol) of $N^1$-benzoyl-$N^2$-[2-[1,4-dihydro-2,6-dimethyl-3-methoxycarbonyl-4-(3-nitrophenyl)-pyridine-5-carboxy]ethyl]-thiourea.

$C_{20}H_{25}IN_4O_6S$ (576.41). Rf ($CH_2Cl_2/CH_3OH$ 90:10): 0.32.

(e)
$N^1$-[2-[1,4-Dihydro-2,6-dimethyl-3-methoxycarbonyl-4-(3-nitrophenyl)-pyridine-5-carboxy]ethyl]-$N^2$-[3-(1H-imidazol-4-yl)propyl]-guanidine hydriodide Prepared by a method analogous to that of Example 1(e) from 1.00 g (1.7 mmol) of S-methyl-N-[2-[1,4-dihydro-2,6-dimethyl-3-methoxycarbonyl-4-(3-nitrophenyl)-pyridine-5-carboxy]ethyl]-isothiuronium iodide and 0.22 g (1.7 mmol) of 3-(1H-imidazol-4-yl)propylamine. 0.73 g (65%) of a yellow, amorphous solid obtained after chromatographic purification on aluminium oxide with ethyl acetate/ethanol (60:40).

$C_{25}H_{32}IN_7O_6$ (653.47). Rf ($CH_3COOC_2H_5/C_2H_5OH$ 60:40): 0.36.

| $^1$H—NMR data (CD$_3$OD, TMS as internal standard): | δ = | 1.7–2.1 | (m) | 2H |
|---|---|---|---|---|
| | | 2.3 | (s) | 3H |
| | | 2.35 | (s) | 3H |
| | | 2.7 | (t) | 2H |
| | | 3.1–3.8 | (m) | 4H |
| | | 3.65 | (s) | 3H |
| | | 4.1–4.4 | (m) | 2H |
| | | 4.9 | (broad) | 6H, replaceable by D$_2$O |
| | | 5.1 | (s) | 1H |
| | | 7.0 | (s) | 1H |
| | | 7.4–8.2 | (m) | 5H ppm. |

Example 4
$N^1$-[2-[1,4-Dihydro-2,6-dimethyl-3-ethoxycarbonyl-4-(3-nitrophenyl)-pyridine-5-carboxy]ethyl]-$N^2$-[3-(1H-imidazol-4-yl)-propyl]-guanidine hydriodide (a)
1,4-Dihydro-2,6-dimethyl-3-ethoxycarbonyl-4-(3-nitrophenyl)-5-(2-phthalimidoethoxy)carbonyl-pyridine Prepared by a method analogous to that of Example 1(a) from 15.80 g (60 mmol) of 2-(3-nitrobenzylidene)-acetoacetic acid ethyl ester and 16.46 g (60 mmol) of 3-amino-crotonic acid-(2-phthalimidoethyl)ester in ethanol. 27.75 g (89%) of yellow crystals melting at 194°–195° C. are obtained.

$C_{27}H_{25}N_3O_8$ (519.51). Rf ($CH_2Cl_2/CH_3OH$ 95:5): 0.48.

(b)
1,4-Dihydro-2,6-dimethyl-3-ethoxycarbonyl-4-(3-nitrophenyl)-5-(2-aminoethoxy)carbonyl-pyridine Prepared by a method analogous to that of Example 1(b) from 20.78 g (40 mmol) of 1,4-dihydro-2,6-dimethyl-3-ethoxycarbonyl-4-(3-nitrophenyl)-5-(2-phthalimidoethoxy)carbonyl-pyridine and 5.83 ml (120 mmol) of hydrazine hydrate. 13.39 g (86%) of yellow crystals, melting point 137°–139° C.

$C_{19}H_{23}N_3O_6$ (389.41). Rf ($CH_2Cl_2/CH_3OH$ 90:10): 0.36.

(c)
$N^1$-Benzoyl-$N^2$-[2-[1,4-dihydro-2,6-dimethyl-3-ethoxycarbonyl-4-(3-nitrophenyl)-pyridine-5-carboxy]ethyl]-thiourea Prepared by a method analogous to that of Example 1(c) from 9.74 g (25 mmol) of 1,4-dihydro-2,6-dimethyl-3-ethoxycarbonyl-4-(3-nitrophenyl)-5-(2-aminoethoxy)-carbonyl-pyridine and 4.08 g (25 mmol) of benzoylisothiocyanate. 12.52 g (91%) of yellow crystals melting at 80°–82° C. obtained from tert.-butyl-methyl ether.

$C_{27}H_{28}N_4O_7S$ (552.60). Rf ($CH_2Cl_2/CH_3OH$ 95:5): 0.62.

(d)
S-Methyl-N-[2-[1,4-dihydro-2,6-dimethyl-3-ethoxycarbonyl-4-(3-nitrophenyl)-pyridine-5-carboxy]ethyl]-isothiuronium iodide By a method analogous to that of Example 1(d) from 11.05 g (20 mmol) of $N^1$-benzoyl-$N^2$-[2-[1,4-dihydro-2,6-dimethyl-3-ethoxycarbonyl-4-(3-nitrophenyl)-pyridine-5-carboxy]ethyl]thiourea and 2.84 g (20 mmol) of methyl iodide. 8.94 g (76%) of a yellow, amorphous foam.

$C_{21}H_{27}IN_4O_6S$ (590.24). Rf ($CH_2Cl_2/CH_3OH$ 90:10): 0.45.

(e)
$N^1$-[2-[1,4-Dihydro-2,6-dimethyl-3-ethoxycarbonyl-4-(3-nitrophenyl)-pyridine-5-carboxy]ethyl]-$N^2$-[3-(1H-imidazol-4-yl)propyl]-guanidine hydriodide 1.00 g (1.69 mmol) of S-methyl-N-[2-[1,4-dihydro-2,6-dimethyl-3-ethoxycarbonyl-4-(3-nitrophenyl)-pyridine-5-carboxy]ethyl]-isothiuronium iodide and 0.21 g (1.69 mmol) of 3-(1H-imidazol-4-yl)propylamine are boiled under reflux in 15 ml of acetonitrile for 3 hours. After removal of the solvent by evaporation under vacuum, the residue is crystallized from dichloromethane. 0.67 g (59%) of a yellow solid melting at 104°–105° C. are obtained.

$C_{26}H_{34}IN_7O_6$ (667.50). Rf ($CH_2Cl_2/CH_3OH$ 80:20): 0.46.

| $^1$H—NMR data (CD$_3$OD, TMS as internal standard) | δ = | 1.2 | (t) | 3H |
|---|---|---|---|---|
| | | 1.7–2.1 | (m) | 2H |
| | | 2.3 | (s) | 3H |
| | | 2.35 | (s) | 3H |
| | | 2.7 | (t) | 2H |
| | | 3.1–3.6 | (m) | 4H |
| | | 4.1 | (q) | 2H |
| | | 4.1–4.4 | (m) | 2H |
| | | 4.8 | (broad) | 6H replaceable by D$_2$O |
| | | 5.1 | (s) | 1H |
| | | 7.0 | (s) | 1H |
| | | 7.4–8.2 | (m) | 5H ppm |

Example 5

$N^1$-[2-[1,4-Dihydro-2,6-dimethyl-3-(2-methoxyethoxy)-carbonyl-4-(3-nitrophenyl)-pyridine-5-carboxy]ethyl]-$N^2$-[3-(1H-imidazol-4-yl)propyl]-guanidine hydriodide

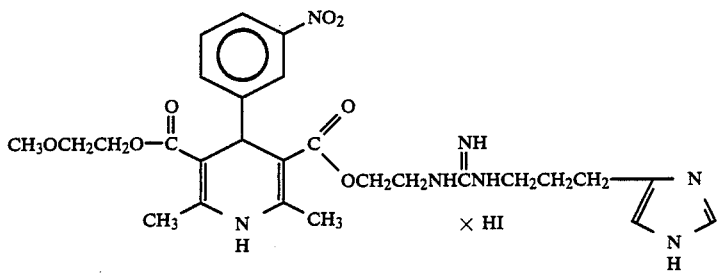

(a) 1,4-Dihydro-2,6-dimethyl-3-(2-methoxyethoxy)-carbonyl-4-(3-nitrophenyl)-5-(2-phthalimidoethoxy)carbonyl-pyridine Prepared by a method analogous to that of Example 1(a) from 7.0 g (24 mmol) of 2-(3-nitrobenzylidene)-acetoacetic acid-(2-methoxyethyl)ester and 6.55 g (24 mmol) of 3-aminocrotonic acid-(2-phthalimidoethyl)ester in ethanol. 11.08 g (84%) of pale yellow crystals, melting point 182°–184° C.

C$_{28}$H$_{27}$N$_3$O$_9$ (549.54). Rf (CH$_2$Cl$_2$/CH$_3$OH 95:5): 0.48.

(b) 1,4-Dihydro-2,6-dimethyl-3-(2-methoxyethoxy)carbonyl-4-(3-nitrophenyl)-5-(2-aminoethoxy)carbonyl-pyridine Prepared by a method analogous to that of Example 1(b) from 10.0 g (18.2 mmol) of 1,4-dihydro-2,6-dimethyl-3-(2-methoxyethoxy)carbonyl-4-(3-nitrophenyl)-5-(2-phthalimidoethoxy)carbonyl-pyridine and 2.65 ml (54.6 mmol) of hydrazine hydrate.

4.0 g (52%) of yellow crystals melting at 136°–137° C. obtained after chromatographic purification on silica gel with dichloromethane/methanol (93:7).

C$_{20}$H$_{25}$N$_3$O$_7$ (419.43). Rf (CH$_2$Cl$_2$/CH$_3$OH 90:10): 0.33.

(c) $N^1$-Benzoyl-$N^2$-[2-[1,4-dihydro-2,6-dimethyl-3-(2-methoxyethoxy)carbonyl-4-(3-nitrophenyl)-pyridine-5-carboxy]ethyl]-thiourea Prepared by a method analogous to that of Example 1(c) from 3.50 g (8.3 mmol) of 1,4-dihydro-2,6-dimethyl-3-(2-methoxyethoxy)carbonyl-4-(3-nitrophenyl)-5-(2-aminoethoxy)carbonyl-pyridine and 1.36 g (8.3 mmol) of benzoyl isothiocyanate. 4.65 g (96%) of a pale yellow oil.

C$_{28}$H$_{30}$N$_4$O$_8$S (582.43). Rf (CH$_2$Cl$_2$/CH$_3$OH 95:5): 0.29.

(d) S-Methyl-N-[2-[1,4-dihydro-2,6-dimethyl-3-(2-methoxyethoxy)carbonyl-4-(3-nitrophenyl)-pyridine-5-carboxy]ethyl]-isothiuronium iodide Prepared from 4.58 g (7.9 mmol) of $N^1$-benzoyl-$N^2$-[2-[1,4-dihydro-2,6-dimethyl-3-(2-methoxyethoxycarbonyl)-4-(3-nitrophenyl)-pyridine-5-carboxy]ethyl]-thiourea by a method analogous to that of Example 1(d). 2.60 g (53%) of a yellow, amorphous solid.

C$_{22}$H$_{29}$IN$_4$O$_7$S (620.43). Rf (CH$_2$Cl$_2$/CH$_3$OH 90:10): 0.55.

(e) $N^1$[2-[1,4-Dihydro-2,6-dimethyl-3-(2-methoxyethoxy)-carbonyl-4-(3-nitrophenyl)-pyridine-5-carboxy]ethyl]-$N^2$-[3-(1H-imidazol-4-yl)propyl]-guanidine hydriodide Prepared by a method analogous to that of Example 1(e) from 1.00 g (1.6 mmol) of S-methyl-N-[2-[1,4-dihydro-2,6-dimethyl-3-(2-methoxyethoxy)carbonyl-4-(3-nitrophenyl)-pyridine-5-carboxy]ethyl]isothiuronium iodide and 0.20 g (1.6 mmol) of 3(1H-imidazol-4-yl)propylamine. 0.51 g (46%) of a yellow solid melting at 94°–96° C.

C$_{27}$H$_{36}$IN$_7$O$_7$ (697.53). Rf (CH$_2$Cl$_2$/CH$_3$OH 80:20): 0.3.

| $^1$H—NMR data (CD$_3$OD, TMS as internal standard) | δ = | 1.7–2.1 | (m) | 2H |
|---|---|---|---|---|
| | | 2.3 | (s) | 3H |
| | | 2.35 | (s) | 3H |
| | | 2.65 | (t) | 2H |
| | | 3.1–3.8 | (m) | 8H |
| | | 3.3 | (s) | 3H |
| | | 4.0–4.4 | (m) | 2H |
| | | 4.8 | (broad) | 6H, replaceable by D$_2$O |
| | | 5.1 | (s) | 1H |
| | | 6.9 | (s) | 1H |
| | | 7.3–8.2 | (m) | 5H ppm. |

Example 6

N[1]-[2-[1,4-Dihydro-2,6-dimethyl-3-isobutoxycarbonyl-4-(2-nitrophenyl)-pyridine-5-carboxy]ethyl]-N[2]-[3-(1H-imidazol-4-yl)propyl]-guanidine hydriodide

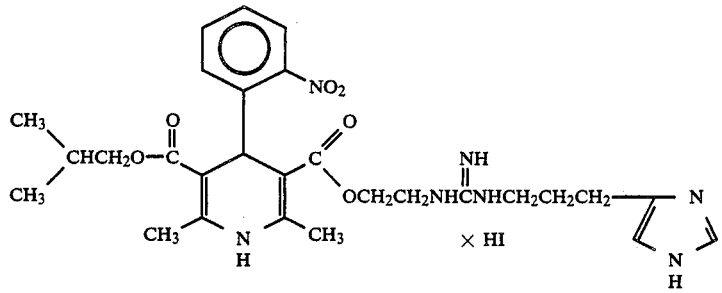

(a)
1,4-Dihydro-2,6-dimethyl-3-isobutoxycarbonyl-4-(2-nitrophenyl)-5-(2-phthalimidoethoxy)carbonyl-pyridine Prepared by a method analogous to that of Example 1(a) from 36.1 g (124 mmol) of 2-(2-nitrobenzylidene)-acetoacetic acid-i-butyl ester and 34.0 g (124 mmol) of 3-amino-crotonic acid-(2-phthalimido-ethyl ester. 44.1 g (69%) of yellow crystals melting at 103°–105° C.

$C_{29}H_{29}N_3O_8$ (547.56). Rf (CH$_2$Cl$_2$/CH$_3$OH 95:5): 0.4.

(b)
1,4-Dihydro-2,6-dimethyl-3-isobutoxycarbonyl-4-(2-nitrophenyl)-5-(2-aminoethoxy)carbonyl-pyridine Prepared by a method analogous to that of Example 1(b) from 10.94 g (20 mmol) of 1,4-dihydro-2,6-dimethyl-3-isobutoxycarbonyl-4-(2-nitrophenyl)-5-(2-phthalimidoethoxycarbonyl)-pyridine and 3.0 ml (60 mmol) of hydrazine hydrate. 8.06 g (96%) of a viscous yellow oil are obtained. This product is used for reactions without further purification.

$C_{21}H_{27}N_3O_6$ (417.46). Rf (CH$_2$Cl$_2$/CH$_3$OH 95:5): 0.2.

(c)
N[1]-Benzoyl-N[2]-[2-[1,4-dihydro-2,6-dimethyl-3-isobutoxycarbonyl-4-(2-nitrophenyl)-pyridine-5-carboxy]ethyl]-thiourea Prepared by a method analogous to that of Example 1(c) from 7.86 g (18.8 mmol) of 1,4-dihydro-2,6-dimethyl-3-isobutoxycarbonyl-4-(2-nitrophenyl)-5-(2-aminoethoxy)carbonyl-pyridine and 3.07 (18.8 mmol) of benzoyl isothiocyanate in ethyl acetate. 9.90 g (91%) of a yellow, amorphous solid.

$C_{29}H_{32}N_4O_7S$ (580.66). Rf (CH$_2$Cl$_2$/CH$_3$OH 95:5): 0.5.

(d)
S-Methyl-N-[2-[1,4-dihydro-2,6-dimethyl-3-isobutoxycarbonyl-4-(2-nitrophenyl)-pyridine-5-carboxy]ethyl]-isothiuronium iodide Prepared by a method analogous to that of Example 1(d) from 3.05 g (5.3 mmol) of N[1]-benzoyl-N[2]-[2-[1,4-dihydro-2,6-dimethyl-3-isobutoxycarbonyl-4-(2-nitrophenyl)-pyridine-5-carboxy]ethyl]-thiourea. 3.10 g (94%) of yellow crystals melting at 107°–109° C. obtained from tert.-butyl-methyl ether.

$C_{23}H_{31}IN_4O_6S$ (618.49). Rf (CH$_2$Cl$_2$/CH$_3$OH 90:10): 0.4.

(e)
N[1]-[2-[1,4-dihydro-2,6-dimethyl-3-isobutoxycarbonyl-4-(2-nitrophenyl)-pyridine-5-carboxy]ethyl]-N[2]-[3-(1H-imidazol-4-yl)propyl]-guanidine hydriodide 1.00 g (1.62 mmol) of S-methyl-N-[2-[1,4-dihydro-2,6-dimethyl-3-isobutoxycarbonyl-4-(2-nitrophenyl)-pyridine-5-carboxy]-ethyl]-isothiuronium iodide and 0.20 g (1.62 mmol) of 3-(1H-imidazol-4-yl)-propylamine are boiled in 20 ml of acetonitrile for 3 hours. After removal of the solvent by evaporation under vacuum, the yellow foam obtained is chromatographed on silica gel with dichloromethane/methanol (85:15) as solvent. 0.68 g (60%) of the title compound is obtained as a yellow, amorphous solid after concentration of the main fraction by evaporation under vacuum.

$C_{28}H_{38}IN_7O_6$ (695.56). Rf (CH$_2$Cl$_2$/CH$_3$OH 80:20): 0.5.

| $^1$H—NMR data (CD$_3$OD, TMS as internal standard) | $\delta =$ | 0.65–0.85 | (2d) | 6H |
|---|---|---|---|---|
| | | 1.7–2.1 | (m) | 3H |
| | | 2.35 | (s) | 6H |
| | | 2.7 | (t) | 2H |
| | | 3.1–4.5 | (m) | 6H |
| | | 3.8 | (d) | 2H |
| | | 4.9 | (broad) | 6H, replaceable by D$_2$O |
| | | 5.8 | (s) | 1H |
| | | 6.95 | (s) | 1H |
| | | 7.3–7.9 | (m) | 5H ppm. |

Example 7

N$^1$-[6[1,4-dihydro-2,6-dimethyl-3-methoxycarbonyl-4-(3-nitrophenyl)-pyridine-5-carboxy]hexyl]-N$^2$[3-(1H-imidazol-4-yl)propyl]-guanidine hydriodide

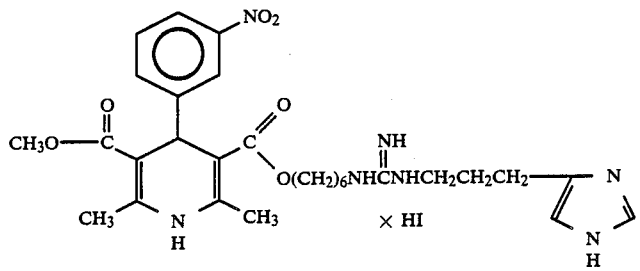

(a)
1,4-Dihydro-2,6-dimethyl-3-methoxycarbonyl-4-(3-nitrophenyl)-5-(6-phthalimidohexyloxy)carbonyl-pyridine 12.0 g (26 mmol) of 2-(3-nitrobenzylidene)-acetoacetic acid-(6-phthalimidohexyl)ester and 3.0 g (26 mmol) of 3-amino-crotonic acid methyl ester are boiled under reflux in 100 ml of isopropanol for 4 hours. After removal of the solvent by evaporation under vacuum, 15.0 g of a brownish yellow oil suitable for reactions without further purification are obtained.

$C_{30}H_{31}N_3O_8$ (561.59). Rf ($CH_2Cl_2/CH_3OH$ 97:3): 0.5.

(b)
1,4-Dihydro-2,6-dimethyl-3-methoxycarbonyl-4-(3-nitrophenyl)-5-(6-aminohexyloxy)carbonyl-pyridine Prepared by a method analogous to that of Example 1(b) from 15.0 g (26 mmol) of 1,4-dihydro-2,6-dimethyl-3-methoxycarbonyl-4-(3-nitrophenyl)-5-(6-phthalimidohexyloxy)carbonyl-pyridine and 3.9 ml (80 mmol) of hydrazine hydrate. 11.2 g (97%) of an orange coloured oil.

$C_{22}H_{29}N_3O_6$ (431.49). Rf ($CH_2Cl_2/CH_3OH/N(C_2H_5)_3$ 90:10:1): 0.2.

(c)
N$^1$-Benzoyl-N$^2$-[6-[1,4-dihydro-2,6-dimethyl-3-methoxycarbonyl-4-(3-nitrophenyl)-pyridine-5-carboxy]hexyl]-thiourea Prepared by a method analogous to that of Example 1(c) from 10.0 g (23 mmol) of 1,4-dihydro-2,6-dimethyl-3-methoxycarbonyl-4-(3-nitrophenyl)-5-(6-aminohexyloxy)carbonyl-pyridine and 3.8 g (23 mmol) of benzoyl isothiocyanate. 10.5 g (76%) of an orange coloured oil are obtained after chromatographic purification on silica gel with dichloromethane/methanol (95:5) as solvent.

$C_{30}H_{34}N_4O_7S$ (594.69). Rf ($CH_2Cl_2/CH_3OH$ 99:1): 0.2.

(d)
S-Methyl-N-[6-[1,4-dihydro-2,6-dimethyl-3-methoxycarbonyl-4-(3-nitrophenyl)-pyridine-5-carboxy]hexyl]-isothiuronium iodide Prepared by a method analogous to that of Example 1(d) from 10.5 g (18 mmol) of N$^1$-benzoyl-N$^2$-[6-[1,4-dihydro-2,6-dimethyl-3-methoxycarbonyl-4-(3-nitrophenyl)-pyridine-5-carboxy]hexyl]-thiourea. 3.66 g (33%) of a yellow, amorphous solid from tert.-butyl methyl ether.

$C_{24}H_{33}IN_4O_6S$ (632.48).
Rf($CH_2Cl_2/CH_3OH/N(C_2H_5)_3$ 90:10:1): 0.3.

(e)
N$^1$-[6-[1,4-Dihydro-2,6-dimethyl-3-methoxycarbonyl-4-(3-nitrophenyl)-pyridine-5-carboxy]hexyl]-N$^2$-[3-(1H-imidazol-4-yl)propyl]-guanidine hydriodide Prepared by a method analogous to that of Example 1(e) from 1.00 g (1.6 mmol) of S-methyl-N-[6-[1,4-dihydro-2,6-dimethyl-3-methoxycarbonyl-4-(3-nitrophenyl)-pyridine-5-carboxy]hexyl]-isothiuronium iodide and 0.20 g (1.6 mmol) of 3-(1H-imidazol-4-yl)propylamine. 1.1 g (97%) of a pale yellow, amorphous solid.

$C_{29}H_{40}IN_7O_6$ (709.59). Rf ($CH_3COOC_2H_5/CH_3OH/NH_4Cl/NH_3$ buffer 50:47.5:2.5): 0.7.

| $^1$H—NMR data (CD$_3$OD, TMS as internal standard) | $\delta =$ | 1.1–2.1 | (m) | 10H |
|---|---|---|---|---|
| | | 2.3 | (s) | 3H |
| | | 2.35 | (s) | 3H |
| | | 2.7 | (t) | 2H |
| | | 3.1–3.5 | (m) | 4H |
| | | 3.7 | (s) | 3H |
| | | 3.9–4.2 | (m) | 2H |
| | | 4.9 | (broad) | 6H, replaceable by D$_2$O |
| | | 5.2 | (s) | 1H |
| | | 7.0 | (s) | 1H |
| | | 7.4–8.3 | (m) | 5H ppm. |

Example 8

N¹-[2-[1,4-Dihydro-2,6-dimethyl-3-methoxycarbonyl-4-(2,3-dichlorophenyl)-pyridine-5-carboxy]ethyl]-N²-[3-(1H-imidazol-4-yl)propyl]-guanidine hydriodide

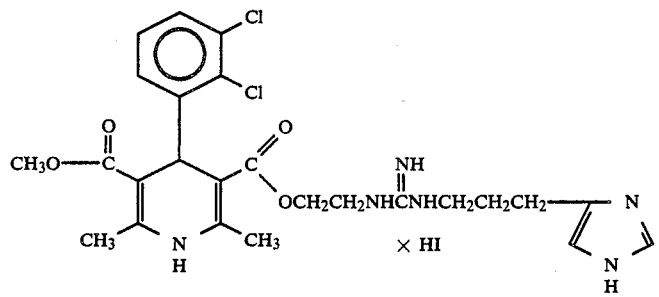

(a)
1,4-Dihydro-2,6-dimethyl-3-methoxycarbonyl-4-(2,3-dichlorophenyl)-5-(2-phthalimidoethoxy)carbonylpyridine Prepared by a method analogous to that of Example 1(a) from 13.0 g (48 mmol) of 2-(2,3-dichlorobenzylidene)-acetoacetic acid methyl ester and 13.1 g (48 mmol) of 3-amino-crotonic acid-(2-phthalimido ethyl)ester. 14.2 g (57%) of pale yellow crystals melting at 195°–196° C.

$C_{26}H_{22}Cl_2N_2O_6$ (529.38). Rf ($CH_2Cl_2/CH_3OH$ 95:5): 0.5.

(b)
1,4-Dihydro-2,6-dimethyl-3-methoxycarbonyl-4-(2,3-dichlorophenyl)-5-(2-aminoethoxy)carbonyl-pyridine Prepared by a method analogous to that of Example 1(b) from 10.0 g (19 mmol) of 1,4-dihydro-2,6-dimethyl-3-methoxycarbonyl-4-(2,3-dichlorophenyl)-5-(2-phthalimidoethoxy)carbonyl-pyridine and 2.84 ml (57 mmol) of hydrazine hydrate. 3.85 g (51%) of pale yellow crystals melting at 166°–167° C. obtained from tert.-butylmethyl ether.

$C_{18}H_{20}Cl_2N_2O_4$ (399.27). Rf ($CH_2Cl_2/CH_3OH$ 80:20): 0.4.

(c)
N¹-Benzoyl-N²-[2-[1,4-dihydro-2,6-dimethyl-3-methoxycarbonyl-4-(2,3-dichlorophenyl)-pyridine-5-carboxyl]ethyl]-thiourea Prepared by a method analogous to that of Example 1(c) from 2.00 g (5 mmol) of 1,4-dihydro-2,6-dimethyl-3-methoxycarbonyl-4-(2,3-dichlorophenyl)-5-(2-aminoethoxy)carbonyl-pyridine and 0.82 g (5 mmol) of benzoyl isothiocyanate. 2.63 g (93%) of an amorphous solid.

$C_{26}H_{25}Cl_2N_3O_5S$ (562.47). Rf ($CH_2Cl_2/CH_3OH$ 90:10): 0.8.

(d)
S-Methyl-N-[2-[1,4-dihydro-2,6-dimethyl-3-methoxycarbonyl-4-(2,3-dichlorophenyl)-pyridine-5-carboxy]ethyl]-iso-thiuronium iodide Prepared by a method analogous to that of Example 1(d) from 2.50 g (4.4 mmol) of N¹-benzoyl-N²-[2-[1,4-dihydro-2,6-dimethyl-3-methoxycarbonyl-4-(2,3-dichlorophenyl)-pyridine-5-carboxy]ethyl]-thiourea. 2.26 g (86%) of a yellow, amorphous solid.

$C_{20}H_{24}Cl_2IN_3O_4S$ (600.30). Rf ($CH_2Cl_2/CH_3OH$ 90:10): 0.3.

(e)
N¹-[2-[1,4-Dihydro-2,6-dimethyl-3-methoxycarbonyl-4-(2,3-dichlorophenyl)-pyridine-5-carboxy]-ethyl]-N²-[3-(1H-imidazol-4-yl)propyl]-guanidine hydriodide Prepared by a method analogous to that of Example 1(e) from 1.00 g (1.67 mmol) of S-methyl-N-[2-[1,4-dihydro-2,6-dimethyl-3-methoxycarbonyl-4-(2,3-dichlorophenyl)-pyridine-5-carboxyl]ethyl]-isothiuronium iodide and 0.21 g (1.67 mmol) of 3-(1H-imidazol-4-yl)propylamine. 0.98 g (87%) of a yellow, amorphous foam.

$C_{25}H_{31}Cl_2IN_6O_4$ (677.42). Rf ($CH_3COOC_2H_5/CH_3OH$ 80:20): 0.2.

| ¹H—NMR data (CD₃OD, TMS as internal standard) | δ = | 1.7–2.1 | (m) | 2H |
|---|---|---|---|---|
| | | 2.25 | (s) | 3H |
| | | 2.3 | (s) | 3H |
| | | 2.7 | (t) | 2H |
| | | 3.1–3.7 | (m) | 4H |
| | | 3.6 | (s) | 3H |
| | | 4.0–4.4 | (m) | 2H |
| | | 4.9 | (broad) | 6H, replaceable by D₂O |
| | | 5.5 | (s) | 1H |
| | | 6.95 | (s) | 1H |
| | | 7.1–7.6 | (m) | 3H |
| | | 7.7 | (s) | 1H ppm |

Example 9

N[1]-[2-[1,4-Dihydro-2,6-dimethyl-3-nitro-4-(2-methylphenyl)-pyridine-5-carboxy]ethyl]-N[2]-[3-(1H-imidazol-4-yl)propyl]-guanidine hydriodide

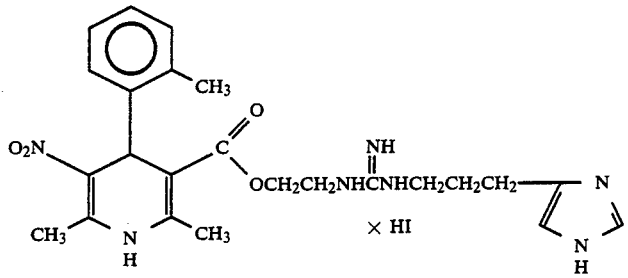

(a)
N[1]-Benzoyl-N[2]-[2-[1,4-dihydro-2,6-dimethyl-3-nitro-4-(2-methylphenyl)-pyridine-5-carboxy]ethyl]-thiourea Prepared by the method of Example 1(c) from 2.49 g (7.5 mmol) of 1,4-dihydro-2,6-dimethyl-3-nitro-4-(2-methylphenyl)-5-(2-aminoethoxy)-carbonyl-pyridine and 1.22 g (7.5 mmol) of benzoyl isothiocyanate. 3.57 g (96%) of yellow crystals melting at 85°–87° C. obtained from tert.-butyl-methyl ether.

$C_{25}H_{26}N_4O_5S$ (494.57). Rf ($CH_2Cl_2/CH_3OH$ 90:10): 0.7.

(b)
S-Methyl-N-[2-[1,4-dihydro-2,6-dimethyl-3-nitro-4-(2-methylphenyl)-pyridine-5-carboxy]ethyl]-isothiuronium iodide Prepared by a method analogous to that of Example 1(d) from 2.52 g (5.1 mmol) of N[1]-benzoyl-N[2]-[2-[1,4-dihydro-2,6-dimethyl-3-nitro-4-(2-methylphenyl)-pyridine-5-carboxy]ethyl]-thiourea. 1.68 g (62%) of a yellow, amorphous solid from tert.-butyl-methylether/dichloromethane (9:1).

$C_{19}H_{25}IN_4O_4S$ (532.40). Rf ($CH_2Cl_2/CH_3OH$ 90:10): 0.25.

(c)
N[1]-[2-[1,4-dihydro-2,6-dimethyl-3-nitro-4-(2-methylphenyl)-pyridine-5-carboxy]ethyl]-N[2]-[3-(1H-imidazol-4-yl)propyl]-guanidine hydriodide Prepared by a method analogous to Example (1e) from 1.00 g (1.88 mmol) of S-methyl-N-[2-[1,4-dihydro-2,6-dimethyl-3-nitro-4-(2-methylphenyl)-pyridine-5-carboxy]ethyl]isothiuronium iodide and 0.23 g (1.88 mmol) of 3-(1H-imidazol-4-yl)propylamine in acetonitrile. 0.65 g (56%) of yellow crystals melting at 85°–87° C.

$C_{24}H_{32}IN_7O_4$ (609.47). Rf ($C_2H_5OH$, $Al_2O_3$ neutral): 0.35.

| $^1$H—NMR data (CD$_3$OD, TMS as internal standard) | δ = | 1.7–2.1 | (m) | 2H |
|---|---|---|---|---|
| | | 2.3 | (s) | 3H |
| | | 2.5 | (s) | 3H |
| | | 2.6 | (s) | 3H |
| | | 2.65 | (t) | 2H |
| | | 3.1–3.6 | (m) | 4H |
| | | 4.0–4.4 | (m) | 2H |
| | | 5.0 | (broad) | 6H, replaceable by D$_2$O |
| | | 5.5 | (s) | 1H |
| | | 6.9 | (s) | 1H |
| | | 6.9–7.3 | (m) | 4H |
| | | 7.6 | (s) | 1H ppm |

Example 10

N[1]-[2-[1,4-Dihydro-2,6-dimethyl-3-nitro-4-(2-trifluoromethylphenyl)-pyridine-5-carboxy]ethyl]-N[2]-[3-(1H-imidazol-4-yl)propyl]-guanidine hydriodide

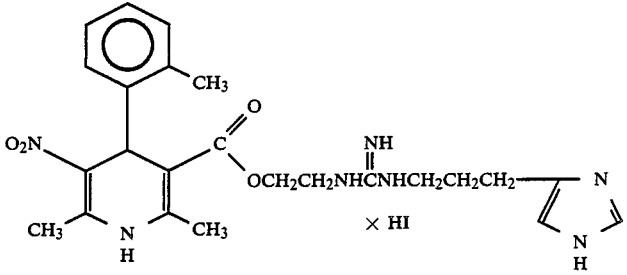

(a)
N[1]-Benzoyl-N[2]-[2-[1,4-dihydro-2,6-dimethyl-3-nitro-4-(2-trifluoromethylphenyl)-pyridine-5-carboxy]ethyl]-thiourea Prepared by a method analogous to that of Example 1(c) from 3.00 g (7.8 mmol) of 1,4-dihydro-2,6-dimethyl-3-nitro-4-(2-trifluoromethylphenyl)-5-(2-aminoethoxy)carbonyl-pyridine and 1.27 g (7.8 mmol) of benzoyl isothiocyanate. 4.01 g (94%) of yellow crystals melting at 83°–85° C.

$C_{25}H_{23}F_3N_4O_5S$ (548.35). Rf ($CH_2Cl_2/CH_3OH$ 95:5): 0.55.

(b)

S-Methyl-N-[2-[1,4-dihydro-2,6-dimethyl-3-nitro-4-(2-trifluoromethylphenyl)-pyridine-5-carboxy]ethyl]-isothiuronium iodide Prepared by a method analogous to that of Example 1(d) from 3.9 g (7.1 mmol) of $N^1$-benzoyl-$N^2$-[2-[1,4-dihydro-2,6-dimethyl-3-nitro-4-(2-trifluoromethylphenyl)-pyridine-5-carboxy]ethyl]-thiourea. 2.23 g (54%) of an amorphous, deep yellow solid obtained from dichloromethane.

$C_{19}H_{22}F_3IN_4O_4S$ (586.37). RF ($CH_2Cl_2/CH_3OH$ 90:10): 0.43.

(c)

$N^1$-[2-[1,4-Dihydro-2,6-dimethyl-3-nitro-4-(2-trifluoromethylphenyl)-pyridine-5-carboxy]ethyl]-$N^2$-[3-(1H-imidazol-4-yl)propyl]-guanidine hydriodide Prepared by a method analogous to that of Example 1(e) from 1.00 g (1.7 mmol) of S-methyl-N-[2-[1,4-dihydro-2,6-dimethyl-3-nitro-4-(2-trifluoromethylphenyl)-pyridine-5-carboxy]ethyl]-isothiuronium iodide and 0.21 g (1.7 mmol) of 3-(1H-imidazol-4-yl)propylamine. 0.40 g (35%) of an orange yellow, amorphous solid.

$C_{24}H_{29}F_3IN_7O_4$ (663.44). Rf ($CH_3COOC_2H_5/C_2H_5OH$ 50:50 on $Al_2O_3$ neutral): 0.28.

| $^1$H—NMR data ($CD_3OD$, TMS as internal standard) | δ = | 1.7–2.1 | (m) | 2H |
|---|---|---|---|---|
| | | 2.35 | (s) | 3H |
| | | 2.5 | (s) | 3H |
| | | 2.7 | (t) | 2H |
| | | 3.2 | (t) | 2H |
| | | 3.45 | (t) | 2H |
| | | 3.9–4.5 | (m) | 2H |
| | | 5.0 | (broad) | 6H, replaceable by $D_2O$ |
| | | 5.95 | (s) | 1H |
| | | 6.9 | (s) | 1H |
| | | 7.2–7.8 | (m) | 5H ppm |

Example 11

$N^1$-[6-[1,4-Dihydro-2,6-dimethyl-3-methoxycarbonyl-4-(2-nitrophenyl)-pyridine-5-carboxy]hexyl]-$N^2$-[3-(1H-imidazol-4-yl)propyl]-guanidine hydriodide

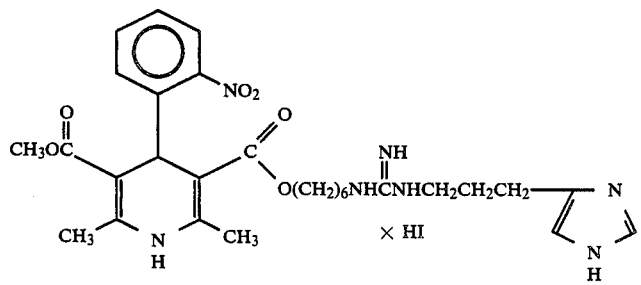

(a)

1,4-Dihydro-2,6-dimethyl-3-methoxycarbonyl-4-(2-nitrophenyl)-5-(6-phthalimidohexyloxy)carbonyl-pyridine Prepared by a method analogous to that of Example 7(a) from 23.0 g (50 mmol) of 2-(2-nitrobenzylidene)-aceto acetic acid-(6-phthalimidohexyl)ester and 5.7 g (50 mmol) of 3-amino-crotonic acid methyl ester. 9.7 g (35%) of a dark yellow oil obtained after column chromatographic purification on silica gel with dichloromethane/methanol (98:2) as solvent.

$C_{30}H_{31}N_3O_8$ (561.59). Rf ($CH_2Cl_2/CH_3OH$ 98:2): 0.3.

(b)

1,4-Dihydro-2,6-dimethyl-3-methoxycarbonyl-4-(2-nitrophenyl)-5-(6-aminohexyloxy)carbonyl-pyridine Prepared by a method analogous to that of Example 1(b) from 9.1 g (16 mmol) of 1,4-dihydro-2,6-dimethyl-3-methoxycarbonyl-4-(2-nitrophenyl)-5-(6-phthalimidohexyloxy)carbonyl-pyridine and 2.4 ml (49 mmol) of hydrazine hydrate. 6.2 g (89%) of an orange coloured oil.

$C_{22}H_{29}N_3O_6$ (431.49). Rf ($CH_2Cl_2/CH_3OH/N(C_2H_5)_3$ 90:10:1): 0.2.

(c)

$N^1$-Benzoyl-$N^2$-[6-[1,4-dihydro-2,6-dimethyl-3-methoxycarbonyl-4-(2-nitrophenyl)-pyridine-5-carboxy]hexyl]-thiourea Prepared from 5.0 g (11.6 mmol) of 1,4-dihydro-2,6-dimethyl-3-methoxycarbonyl-4-(2-nitrophenyl)-5-(6-aminohexyloxy)carbonyl-pyridine and 1.9 g (11.6 mmol) of benzoylisothiocyanate by a method analogous to that of Example 1(c). 4.7 g (68%) of an orange yellow, amorphous solid are obtained after chromatographic purification on silica gel with dichloromethane/methanol (95:5) as solvent.

$C_{30}H_{34}N_4O_7S$ (594.69). Rf ($CH_2Cl_2/CH_3OH$ 95:5): 0.7.

(d)

S-Methyl-N-[6-[1,4-dihydro-2,6-dimethyl-3-methoxycarbonyl-4-(2-nitrophenyl)-pyridine-5-carboxy]hexyl]-isothiuronium iodide Prepared by a method analogous to that of Example 7(d) from 6.9 g (11.6 mmol) of $N^1$-benzoyl-$N^2$-[6-[1,4-dihydro-2,6-dimethyl-3-methoxycarbonyl-4-(2-nitrophenyl)-pyridine-5-carboxy]hexyl]-thiourea. 2.7 g (37%) of a yellow, amorphous solid.

$C_{24}H_{33}IN_4O_6S$ (632.48). Rf ($CH_2Cl_2/CH_3OH/N(C_2H_5)_3$ 90:10:1): 0.4.

(e)

$N^1$-[6-[1,4-Dihydro-2,6-dimethyl-3-methoxycarbonyl-4-(2-nitrophenyl)-pyridine-5-carboxy]hexyl]-$N^2$-[3-(1H-imidazol-4-yl)propyl]-guanidine hydriodide Prepared by a method analogous to that of Example 1(e) from 1.00 g (1.6 mmol) of S-methyl-N-[6-[1,4-dihydro-2,6-dimethyl-3-methoxycarbonyl-4-(2-nitrophenyl)-pyridine-5-carboxy]hexyl]-isothiuronium iodide and 0.20 g (1.6 mmol) of 3-(1H-imidazol-4-yl)-propylamine. 0.98 g (87%) of a yellow, amorphous solid.

$C_{29}H_{40}IN_7O_6$ (709.59). Rf ($CH_3COOC_2H_5$/$CH_3OH$/$NH_4Cl$/$NH_3$ buffer (50:47.5:2.5): 0.7.

| $^1$H—NMR data (CD$_3$OD, TMS as internal standard) | δ = | 1.1–1.8 | (m) | 8H |
| | | 1.8–2.1 | (m) | 2H |
| | | 2.3 | (s) | 3H |
| | | 2.4 | (s) | 3H |
| | | 2.7 | (t) | 2H |
| | | 3.1–3.4 | (m) | 4H |
| | | 3.6 | (s) | 3H |
| | | 3.9–4.2 | (m) | 2H |
| | | 4.8 | (broad) | 6H, replaceable by D$_2$O |
| | | 5.8 | (s) | 1H |
| | | 6.95 | (s) | 1H |
| | | 7.2–7.9 | (m) | 5H ppm. |

Example 12

3-[1,4-Dihydro-2,6-dimethyl-3-methoxycarbonyl-4-(2-nitrophenyl)-pyridine-5-carboxy]-N-[3-(1H-imidazol-4-yl)propyl]-propionamidine hydrochloride

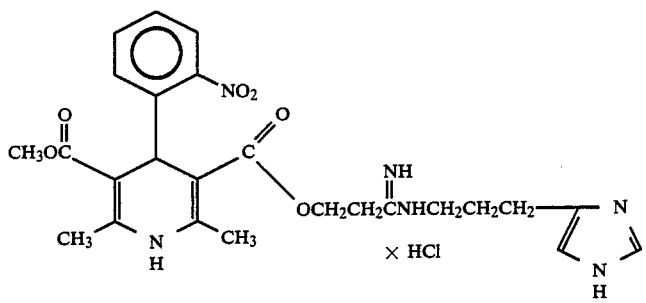

(a) 1,4-Dihydro-2,6-dimethyl-3-methoxycarbonyl-4-(2-nitrophenyl)-5-(2-cyanoethoxy)-carbonyl-pyridine

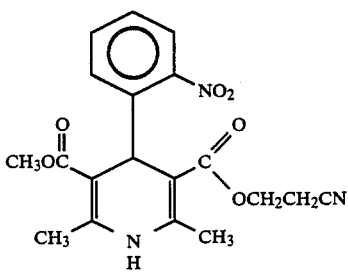

Prepared by a method analogous to that of Example 1(a) from 24.9 g (100 mmol) of 2-(2-nitrobenzylidene)acetoacetic acid methyl ester and 15.4 g (100 mmol) of 3-amino-crotonic acid-(2-cyanoethyl)ester in ethanol. 23.8 g (62%) of pale yellow crystals melting at 153°–154° C. obtained after recrystallisation from methanol.

$C_{19}H_{19}N_3O_6$ (385.38). Rf ($CH_2Cl_2$/$C_2H_5OH$ 97:3): 0.42.

(b) 3-[1,4-Dihydro-2,6-dimethyl-3-methoxycarbonyl-4-(2-nitrophenyl)-pyridine-5-carboxy]-propionimidic acid methyl ester dihydrochloride

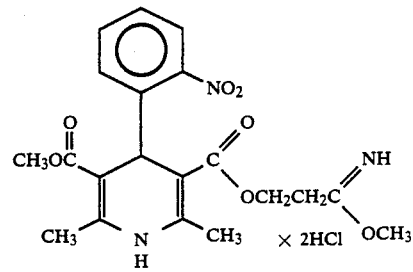

5.0 g (13 mmol) of 1,4-Dihydro-2,6-dimethyl-3-methoxycarbonyl-4-(2-nitrophenyl)-5-(2-cyanoethoxy)-carbonyl-pyridine are dissolved in 15 ml of anhydrous methanol and 20 ml of dichloromethane and cooled to 0° C. Anhydrous hydrogen chloride gas is then introduced at a reaction temperature of 0° to 5° C. until saturation point is reached (about 3 hours). The solution obtained is kept at 0° C. for 20 hours and then concentrated by evaporation at a bath temperature of at the most 20° C. The residue is taken up twice with 20 ml portions of dichloromethane and concentrated by evaporation under vacuum. 6.4 g of a yellow, hygroscopic foam are obtained as residue which is used for further reactions without further purification.

$C_{20}H_{25}Cl_2N_3O_7$ (490.34). Rf ($CH_2Cl_2$/$CH_3OH$/$N(C_2H_5)_3$ 90:10:1): 0.6.

(c) 3-[1,4-Dihydro-2,6-dimethyl-3-methoxycarbonyl-4-(2-nitrophenyl)-pyridine-5-carboxy]-N-[3-(1H-imidazol-4-yl)-propyl]-propionamidine hydrochloride 5.9 g (12 mmol) of 3-[1,4-dihydro-2,6-dimethyl-3-methoxycarbonyl-4-(2-nitrophenyl)-pyridine-5-carboxy]-propionimidic acid methyl ester dihydrochloride and 1.51 g (12 mmol) of 3-(1H-imidazol-4-yl)propylamine are stirred togther in 50 ml of methanol at room temperature for 30 hours. The amorphous, crude product obtained after removal of the solvent by evaporation under vacuum is purified by chromatography on silica gel with ethyl acetate/methanol (70:30) as solvent. The main fraction yields 2.05 g (31%) of a yellow, amorphous solid after concentration by evaporation under vacuum.

$C_{25}H_{31}ClN_6O_6$ (547.01). Rf ($CH_3COOC_2H_5$/$CH_3OH$ 70:30): 0.3.

| $^1$H—NMR data (CD$_3$OD, TMS as internal standard) | δ = | 1.8–2.2 | (m) | 2H |
|---|---|---|---|---|
| | | 2.3 | (s) | 3H |
| | | 2.35 | (s) | 3H |
| | | 2.6–3.0 | (m) | 4H |
| | | 3.2–3.5 | (t) | 2H |
| | | 3.55 | (s) | 3H |
| | | 4.0–4.8 | (m) | 2H |
| | | 5.1 | (broad) | 5H, replaceable by D$_2$O |
| | | 5.7 | (s) | 1H |
| | | 6.95 | (s) | 1H |
| | | 7.2–7.9 | (m) | 5H ppm |

Example 13

3-[1,4-Dihydro-2,6-dimethyl-3-methoxycarbonyl-4-(2-nitrophenyl)-pyridine-5-carboxy]-N-[2-(1H-imidazol-4-yl)ethyl]-propionamidine hydrochloride

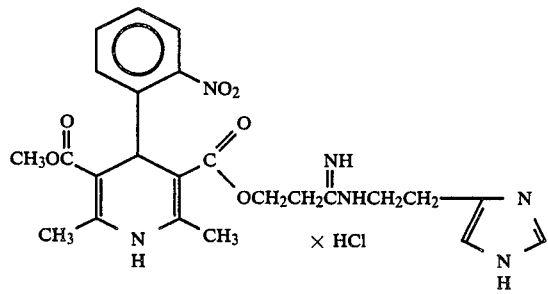

Prepared by a method analogous to that of Example 12(c) from 0.65 g (1.3 mmol) of 3-[1,4-dihydro-2,6-dimethyl-3-methoxycarbonyl-4-(2-nitrophenyl)-pyridine-5-carboxy]-propionimidic acid methyl ester dihydrochloride and 0.15 g (1.3 mmol) of 2-(1H-imidazol-4-yl)-ethylamine. 0.20 g (28%) of a yellow, amorphous solid is obtained after chromatographic purification on silica gel with ethyl acetate/methanol (70:30) as solvent.

C$_{24}$H$_{29}$ClN$_6$O$_6$ (533.00). Rf (CH$_3$COOC$_2$H$_5$/CH$_3$OH 50:50): 0.5.

| $^1$H—NMR data (CD$_3$OD, TMS as internal standard) | δ = | 2.3 (s) | 3H |
|---|---|---|---|
| | | 2.35 (s) | 3H |
| | | 2.7–3.1 (m) | 4H |
| | | 3.5 (t) | 2H |
| | | 3.55 (s) | 3H |
| | | 4.0–4.7 (m) | 2H |
| | | 5.0 (broad) | 5H, replaceable by D$_2$O |
| | | 5.7 (s) | 1H |
| | | 7.0 (s) | 1H |
| | | 7.2–7.8 (m) | 5H ppm |

Example 14

4-[1,4-Dihydro-2,6-dimethyl-3-methoxycarbonyl-4-(2-nitrophenyl)-pyridine-5-carboxy]-N-[3-(1H-imidazol-4-yl)propyl]-butyramidine hydrochloride

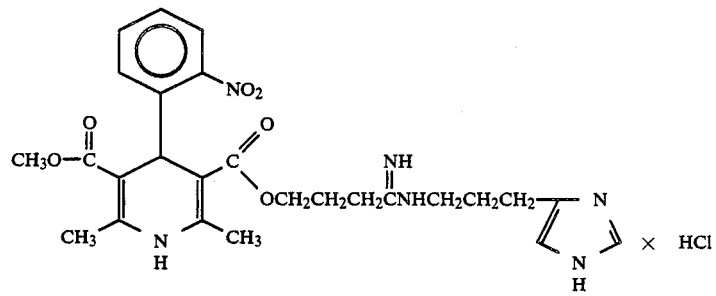

(a)
1,4-Dihydro-2,6-dimethyl-3-methoxycarbonyl-4-(2-nitrophenyl)-5-(3-chloropropoxy)-carbonyl-pyridine 8.93 g (50 mmol) of acetoacetic acid-(3-chloropropyl)ester and 4.00 g (50 mmol) of ammonium acetate are boiled under reflux in 50 ml of ethanol in a nitrogen atmosphere for 1.5 hours. After the addition of 12.50 g (50 mmol) of 2-(2-nitrobenzylidene)-acetoacetic acid methyl ester, boiling is continued for 12 hours. The solution is then concentrated by evaporation under vacuum and the residue obtained is chromatographically purified on silica gel with dichloromethane/methanol (95:5) as solvent. Concentration of the polar, yellow main fraction by evaporation under vacuum yields 4.10 g (20%) of a yellow oil.

C$_{19}$H$_{21}$ClN$_2$O$_6$ (408.84). Rf (CH$_2$Cl$_2$/CH$_3$OH 95:5): 0.7.

(b)
1,4-Dihydro-2,6-dimethyl-3-methoxycarbonyl-4-(2-nitrophenyl)-5-(3-cyanopropoxy)carbonyl-pyridine 0.55 g (11 mmol) of sodium cyanide in 15 ml of dimethylsulphoxide are added dropwise at a reaction temperature of 60° C. to a solution of 4.09 g (10 mmol) of 1,4-dihydro-2,6-dimethyl-3-methoxycarbonyl-4-(2-nitrophenyl)-5-(3-chloropropoxy)carbonyl-pyridine in 10 ml of dimethylsulphoxide. The reaction mixture is then stirred for 2.5 hours at 120° C. and is poured into 150 ml of ice water after it has cooled down. The mixture is extracted with 3×50 ml of ethyl acetate. After dehydration and concentration of the organic phases by evaporation under vacuum, 5.7 g of a brown oil are obtained. This oil is chromatographed on silica gel with dichloromethane/methanol (99:1). After concentration by evaporation under vacuum and recrystallisation of the residue from methanol, the main fraction yields 2.7 g (68%) of yellow crystals, melting point 48°–51° C.

C$_{20}$H$_{21}$N$_3$O$_6$ (399.40). Rf (CH$_2$Cl$_2$/CH$_3$OH 95:5): 0.5.

(c)
4-[1,4-Dihydro-2,6-dimethyl-3-methoxycarbonyl-4-(2-nitrophenyl)-pyridine-5-carboxy]-butyrimidic acid-methyl ester dihydrochloride 2.6 g (89%) of a yellow foam which can be used for reactions without further purification are obtained from 2.30 g (5.8 mmol) of 1,4-dihydro-2,6-dimethyl-3-methoxycarbonyl-4-(2-nitrophenyl)-5-(3-cyanopropoxy)carbonyl-pyridine by a method analogous to that of Example 12(b)

$C_{21}H_{27}Cl_2N_3O_7$ (504.36). Rf $(CH_2Cl_2/CH_3OH/N(C_2H_5)_3$ 90:10:1): 0.6.

(d)
4-[1,4-Dihydro-2,6-dimethyl-3-methoxycarbonyl-4-(2-nitrophenyl)-pyridine-5-carboxy]-N-[3-(1H-imidazol-4-yl)propyl]-butyramidine hydrochloride Prepared by a method analogous to that of Example 12(c) from 1.00 g (2 mmol) of 4-[1,4-dihydro-2,6-dimethyl-3-methoxycarbonyl-4-(2-nitrophenyl)-pyridine-5-carboxy]-butyrimidic acid methyl ester dihydrochloride and 0.25 g (2 mmol) of 3-(1H-imidazol-4-yl)propylamine. 0.30 g (27%) of a yellow, solidified foam obtained after chromatographic purification on silica gel with ethyl acetate/methanol (70:30) as solvent.

$C_{26}H_{33}ClN_6O_6$ (561.03). Rf $(CH_3COOC_2H_5/CH_3OH$ 1:1): 0.4.

| $^1$H—NMR data (CD$_3$OD, TMS as internal standard): | δ = 1.8–2.2 (m) | 4H |
|---|---|---|
| | 2.3 (s) | 3H |
| | 2.35 (s) | 3H |
| | 2.4–2.9 (m) | 4H |
| | 3.4 (t) | 2H |
| | 3.6 (s) | 3H |
| | 3.8–4.5 (m) | 2H |
| | 5.0 (broad) | 5H, replaceable by D$_2$O |
| | 5.8 (s) | 1H |
| | 7.0 (s) | 1H |
| | 7.2–7.9 (m) | 5H ppm. |

Example 15
$N^1$-[4-[1,4-Dihydro-2,6-dimethyl-3-methoxycarbonyl-4-(2-nitrophenyl)-pyridine-5-carboxy]butyl]-$N^2$-[3-(1H-imidazol-4-yl)propyl]-guanidine hydriodide

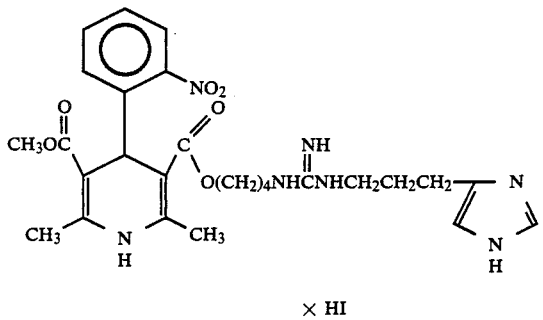

× HI

(a)
1,4-Dihydro-2,6-dimethyl-3-methoxycarbonyl-4-(2-nitrophenyl)-5-(4-phthalimido-butoxy)carbonyl-pyridine 13.7 g (55 mmol) of 2-(2-nitrobenzylidene)-acetoacetic acid methyl ester and 16.6 g (55 mmol) of 3-aminocrotonic acid-(4-phthalimido-butyl)ester are boiled in 150 ml of ethanol for 18 hours. The orange yellow oil (28.7 g-98%) obtained after removal of the solvent by evaporation under vacuum is used for further reactions without further purification.

$C_{28}H_{27}N_3O_8$ (533.54). Rf $(CH_2Cl_2/CH_3OH$ 97:3): 0.44.

(b)
1,4-Dihydro-2,6-dimethyl-3-methoxycarbonyl-4-(2-nitrophenyl)-5-(4-aminobutoxy)carbonyl-pyridine Prepared by a method analogous to that of Example 1(b) from 27.0 g (51 mmol) of 1,4-dihydro-2,6-dimethyl-3-methoxycarbonyl-4-(2-nitrophenyl)-5-(4-phthalimidobutoxy)carbonyl-pyridine and 7.4 ml (152 mmol) of hydrazine hydrate. 16.0 g (78%) of an orange yellow oil obtained after chromatographic purification on silica gel with dichloromethane/methanol (95:5) as solvent.

$C_{20}H_{25}N_3O_6$ (403.44). Rf $(CH_2Cl_2/CH_3OH/NH_3$ conc. 50:50:1): 0.38.

(c)
$N^1$-Benzoyl-$N^2$-[4-[1,4-dihydro-2,6-dimethyl-3-methoxycarbonyl-4-(2-nitrophenyl)-pyridine-5-carboxy]butyl]-thiourea By a method analogous to that of Example 1(c) from 6.50 g (16 mmol) of 1,4-dihydro-2,6-dimethyl-3-methoxycarbonyl-4-(2-nitrophenyl)-5-(4-aminobutoxy)carbonyl-pyridine and 2.63 g (16 mmol) of benzoyl isothiocyanate. 4.38 g (48%) of a pale yellow, amorphous solid obtained after column chromatography on silica gel with dichloromethane/methanol (98:2) as solvent.

$C_{28}H_3N_4O_7S$ (566.44). Rf $(CH_2Cl_2/CH_3OH$ 95:5): 0.75.

(d)
S-Methyl-N-[4-[1,4-dihydro-2,6-dimethyl-3-methoxycarbonyl-4-(2-nitrophenyl)-pyridine-5-carboxy]butyl]-isothiuronium iodide From 3.5 g (6.2 mmol) of $N^1$-benzoyl-$N^2$-[4-[1,4-dihydro-2,6-dimethyl-3-methoxycarbonyl-4-(2-nitrophenyl)-pyridine-5-carboxy]butyl]-thiourea by a method analogous to that of Example 1(d). 3.15 g (84%) of a pale yellow, amorphous solid.

$C_{22}H_{29}IN_4O_6S$ (604.46). Rf $(CH_3COOC_2H_5/CH_3OH$ 70:30): 0.73.

(e)
$N^1$-[4-[1,4-Dihydro-2,6-dimethyl-3-methoxycarbonyl-4-(2-nitrophenyl)-pyridine-5-carboxy]butyl]-$N^2$-[3-(1H-imidazol-4-yl)propyl]-guanidine hydroiodide Prepared by a method analogous to that of Example 1(e) from 1.00 g (1.65 mmol) of S-methyl-N-[4-[1,4-dihydro-2,6-dimethyl-3-methoxycarbonyl-4-(2-nitrophenyl)pyridine-5-carboxy]butyl]-isothiuronium iodide and 0.21 g (1.65 mmol) of 3-(1H-imidazol-4-yl)propylamine. 0.36 g (32%) of a yellow, amorphous solid.

$C_{27}H_{36}IN_7O_6$ (681.53). Rf $(CH_3COOC_2H_5/CH_3OH$ 70:30): 0.46.

| $^1$H—NMR data (CD$_3$OD, TMS as internal standard) | δ = 1.3–1.7 (m) | 4H |
|---|---|---|
| | 1.8–2.2 (m) | 2H |
| | 2.3 (s) | 3H |
| | 2.4 (s) | 3H |
| | 2.6–2.9 (t) | 2H |
| | 3.1–3.5 (m) | 4H |
| | 3.6 (s) | 3H |

| | |
|---|---|
| 3.9–4.3 (m) | 2H |
| 4.9 (broad) | 6H, replaceable by D$_2$O |
| 5.75 (s) | 1H |
| 7.05 (s) | 1H |
| 7.2–8.0 (m) | 5H ppm. |

Example 16

N$^1$-[4-[1,4-Dihydro-2,6-dimethyl-3-methoxycarbonyl-4-(3-nitrophenyl)-pyridine-5-carboxy]butyl]-N$^2$-[3-(1H-imidazol-4-yl)propyl]-guanidine hydriodide

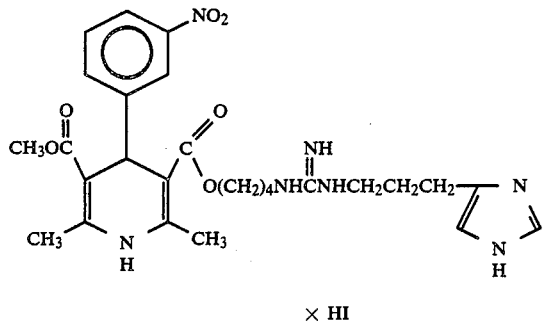

× HI

(a)

1,4-Dihydro-2,6-dimethyl-3-methoxycarbonyl-4-(3-nitrophenyl)-5-(4-phthalimido-butoxy)-carbonyl-pyridine 6.14 g (35%) of a yellow oil are obtained by a method analogous to that of Example 15(a) from 8.25 g (33 mmol) of 2-(3-nitrobenzylidene)-acetoacetic acid methyl ester and 10.00 g (33 mmol) of 3-amino-crotonic acid-(4-phthalimido-butyl)ester after 18 hours' boiling in 85 ml of ethanol followed by chromatographic purification of the crude product on silica gel with dichloromethane/methanol (95:5) as solvent.

C$_{28}$H$_{27}$N$_3$O$_8$ (533.54). Rf (CH$_2$Cl$_2$/CH$_3$OH 95:5): 0.67.

(b)

1,4-Dihydro-2,6-dimethyl-3-methoxycarbonyl-4-(3-nitrophenyl)-5-(4-aminobutoxy)-carbonyl-pyridine Obtained by a method analogous to that of Example 1(b) from 5.0 g (9.4 mmol) of 1,4-dihydro-2,6-dimethyl-3-methoxycarbonyl-4-(3-nitrophenyl)-5-(4-phthalimidobutoxy)-carbonyl-pyridine and 1.4 ml (28 mmol) of hydrazine hydrate. 3.6 g (95%) of a yellow oil which is used for further reactions without purification.

C$_{20}$H$_{25}$N$_3$O$_6$ (403.44). Rf (CH$_2$Cl$_2$/CH$_3$OH 80:20): 0.3.

(c)

N$^1$-Benzoyl-N$^2$-[4-[1,4-dihydro-2,6-dimethyl-3-methoxycarbonyl-4-(3-nitrophenyl)-pyridine-5-carboxy]butyl]-thiourea Prepared by a method analogous to that of Example 1(c) from 3.60 g (9 mmol) of 1,4-dihydro-2,6-dimethyl-3-methoxycarbonyl-4-(3-nitrophenyl)-5-(4-aminobutoxy)carbonyl-pyridine and 1.45 g (9 mmol) of benzoyl isothiocyanate. Column chromatography on silica gel using dichloromethane/methanol (97:3) as solvent yields 2.71 g (51%) of an orange yellow, viscous oil.

C$_{28}$H$_{30}$N$_4$O$_7$S (566.44). Rf (CH$_2$Cl$_2$/CH$_3$OH 99:1): 0.58.

(d)

S-Methyl-N-[4-[1,4-dihydro-2,6-dimethyl-3-methoxycarbonyl-4-(3-nitrophenyl)-pyridine-5-carboxy]butyl]-isothiuronium iodide Obtained as a pale yellow, amorphous solid from 2.0 g (3.5 mmol) of N$^1$-benzoyl-N$^2$-[4-[1,4-dihydro-2,6-dimethyl-3-methoxycarbonyl-4-(3-nitrophenyl)-pyridine-5-carboxy]butyl]-thiourea by the method described in Example 1(d). Yield: 1.8 g (84%).

C$_{22}$H$_{29}$IN$_4$O$_6$S (604.46). Rf (CH$_2$Cl$_2$/CH$_3$OH 90:10): 0.55.

(e)

N$^1$-[4-[1,4-Dihydro-2,6-dimethyl-3-methoxycarbonyl-4-(3-nitrophenyl)-pyridine-5-carboxy]butyl]-N$^2$-[3-(1H-imidazol-4-yl)propyl]-guanidine hydriodide 1.00 g (1.65 mmol) of S-methyl-N-[4-[1,4-dihydro-2,6-dimethyl-3-methoxycarbonyl-4-(3-nitrophenyl)-pyridine-5-carboxy]butyl]-isothiuronium iodide and 0.21 g (1.65 mmol) of 3-(1H-imidazol-4-yl)propylamine are boiled in 15 ml of acetonitrile for 3 hours. The reaction mixture is worked up as described in Example 1(e) and yields 0.18 g (16%) of a pale yellow, amorphous solid.

C$_{27}$H$_{36}$IN$_7$O$_6$ (681.53). Rf (CH$_3$COOC$_2$H$_5$/CH$_3$OH/NH$_4$Cl/NH$_3$ buffer 70:28:2): 0.3.

| | | |
|---|---|---|
| $^1$H NMR data: (CD$_3$OD, TMS as internal standard) | δ = 1.4–2.1 (m) | 6H |
| | 2.3 (s) | 3H |
| | 2.35 (s) | 3H |
| | 2.7 (t) | 2H |
| | 3.1–3.4 (m) | 4H |
| | 3.6 (s) | 3H |
| | 3.9–4.2 (m) | 2H |
| | 4.9 (broad) | 6H, replaceable by D$_2$O |
| | 5.1 (s) | 1H |
| | 6.9 (s) | 1H |
| | 7.4–8.2 (m) | 5H ppm. |

Example 17

N$^1$-[5-[1,4-Dihydro-2,6-dimethyl-3-methoxycarbonyl-4-(2-nitrophenyl)-pyridine-5-carboxy]pentyl]-N$^2$-[3-(1H-imidazol-4-yl)propyl]-guanidine hydriodide

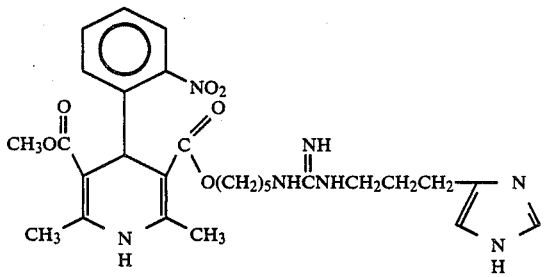

× HI

Prepared by a method analogous to that of Example 1(e) from 1.00 g (1.62 mmol) of S-methyl-N-[5-[1,4-dihydro-2,6-dimethyl-3-methoxycarbonyl-4-(2-nitrophenyl)-pyridine-5-carboxy]pentyl]-isothiuronium iodide and 0.20 g (1.62 mmol) of 3-(1H-imidazol-4- yl)propylamine, 0.28 g (25%) of a pale yellow, amorphous solid.

$C_{28}H_{38}IN_7O_6$ (695.56). Rf ($CH_3COOC_2H_5$/$CH_3OH$/$NH_4Cl$/$NH_3$ buffer 50:47.5:2.5): 0.50.

| $^1H$—NMR data: (CD$_3$OD, TMS as internal standard) | δ = 1.2–2.2 (m) | 8H |
| --- | --- | --- |
| | 2.3 (s) | 3H |
| | 2.4 (s) | 3H |
| | 2.7 (t) | 2H |
| | 3.1–3.4 (m) | 4H |
| | 3.6 (s) | 3H |
| | 3.9–4.3 (m) | 2H |
| | 4.9 (broad) | 6H, replaceable by D$_2$O, |
| | 5.8 (s) | 1H |
| | 7.0 (s) | 1H |
| | 7.3–7.9 (m) | 5H ppm. |

Example 18

$N^1$-[5-[1,4-dihydro-2,6-dimethyl-3-methoxycarbonyl-4-(3-nitrophenyl)-pyridine-5-carboxy]pentyl]-$N^2$-[3-(1H-imidazol-4-yl)propyl]-guanidine hydroiodide

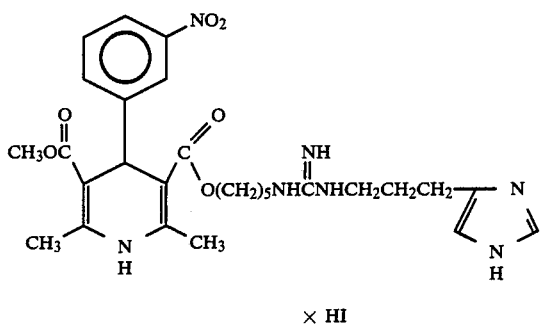

× HI

Prepared by a method analogous to that of Example 1(e) from 1.00 g (1.62 mmol) of S-methyl-N-[5-[1,4-dihydro-2,6-dimethyl-3-methoxycarbonyl-4-(3-nitrophenyl)-pyridine-5-carboxy]pentyl]-isothiuronium iodide and 0.20 g (1.62 mmol) of 3-(1H-imidazol-4-yl)propylamine. 0.32 g (28%) of a pale yellow, amorphous solid.

$C_{28}H_{38}IN_7O_6$ (695.56). Rf ($CH_3COOC_2H_5$/$CH_3OH$/$NH_4cl$/$NH_3$ buffer 50:47.5:2.5): 0.48.

| $^1H$—NMR data: (CD$_3$OD, TMS as internal standard) | δ = 1.2–2.1 (m) | 8H |
| --- | --- | --- |
| | 2.35 (s) | 3H |
| | 2.4 (s) | 3H |
| | 2.7 (t) | 2H |
| | 3.1–3.4 (m) | 4H |
| | 3.7 (s) | 3H |
| | 4.0–4.2 (m) | 2H |
| | 4.9 (broad) | 6H, replaceable by D$_2$O, |
| | 5.15 (s) | 1H |
| | 6.95 (s) | 1H |
| | 7.4–8.2 (m) | 5H, ppm. |

Example 19

$N^1$-[6-[1,4-Dihydro-2,6-dimethyl-3-methoxycarbonyl-4-(2,3-dichlorophenyl)-pyridine-5-carboxy]hexyl]-$N^2$-[3-(1H-imidazol-4-yl)propyl]-guanidine hydriodide

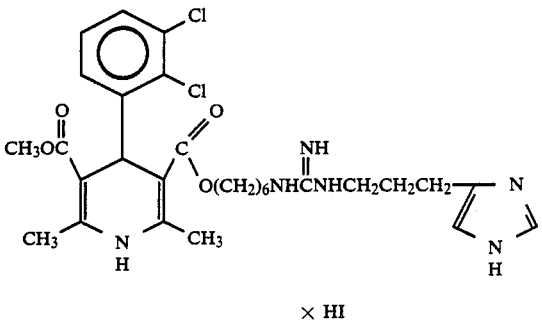

× HI (a)

1,4-Dihydro-2,6-dimethyl-3-methoxycarbonyl-4-(2,3-dichlorophenyl)-5-(6-phthalimido-hexyloxy)-carbonyl-pyridine 14.15 g (quantitative) of a reddish yellow oil are obtained from 6.62 g (24 mmol) of 2-(2,3-dichlorobenzylidene)-acetoacetic acid methyl ester and 8.00 g (24 mmol) of 3-amino-crotonic acid-(6-phthalimidohexyl)ester by a method analogous to that of Example 1(a). The oil obtained is used as crude product for further reactions.

$C_{30}H_{30}Cl_2N_2O_6$ (585.48). Rf ($CH_2Cl_2$/$CH_3OH$ 98:2): 0.53.

(b)

1,4-Dihydro-2,6-dimethyl-3-methoxycarbonyl-4-(2,3-dichlorophenyl)-5-(6-aminohexyloxy)-carbonyl-pyridine Prepared by a method analogous to that of Example 1(b) from 11.0 g (19 mmol) of 1,4-dihydro-2,6-dimethyl-3-methoxycarbonyl-4-(2,3-dichlorophenyl)-5-(6-phthalimido-hexyloxy)carbonyl-pyridine and 2.8 ml (56 mmol) of hydrazine hydrate. The crude product is used for further reactions without purification.

$C_{22}H_{28}Cl_2N_2O_4$ (455.38). Rf ($CH_2Cl_2$/$CH_3OH$ 80:20): 0.17.

(c)

$N^1$-Benzoyl-$N^2$-[6-[1,4-dihydro-2,6-dimethyl-3-methoxycarbonyl-4-(2,3-dichlorophenyl)-pyridine-5-carboxy]-hexyl]-thiourea Prepared by a method analogous to that of Example 1(c) from 8.0 g (17.6 mmol) of 1,4-dihydro-2,6-dimethyl-3-methoxycarbonyl-4-(2,3-dichlorophenyl)-5-(6-aminohexyloxy)carbonyl-pyridine and 2.9 g (17.6 mmol) of benzoylisothiocyanate. 6.9 g (63%) of a yellow, amorphous solid is obtained after column chromatography on silica gel with dichloromethane/methanol (98:2) as solvent.

$C_{30}H_{33}Cl_2N_3O_5S$ (618.58). Rf ($CH_2Cl_2$/$CH_3OH$ 98:2): 0.40.

(d)
S-Methyl-N-[6-[1,4-dihydro-2,6-dimethyl-3-methoxycarbonyl-4-(2,3-dichlorophenyl)-pyridine-5-carboxy]-hexyl]-isothiuronium iodide Prepared by a method analogous to that of Example 1(d) from 5.0 g (8.1 mmol) of $N^1$-benzoyl-$N^2$-[6-[1,4-dihydro-2,6-dimethyl-3-methoxycarbonyl-4-(2,3-dichlorophenyl)-pyridine-5-carboxy]hexyl]-thiourea. 3.7 g (86%) of a yellow, amorphous solid.

$C_{24}H_{32}Cl_2IN_3O_4S$ (656.41). Rf ($CH_2Cl_2/CH_3OH$ 90:10): 0.33.

(e)
$N^1$-[6-[1,4-Dihydro-2,6-dimethyl-3-methoxycarbonyl-4-(2,3-dichlorophenyl)-pyridine-5-carboxy]hexyl]-$N^2$-[3-(1H-imidazol-4-yl)propyl]-guanidine hydriodide Prepared by a method analogous to that of Example 1(e) from 1.50 g (2.8 mmol) of S-methyl-N-[6-[1,4-dihydro-2,6-dimethyl-3-methoxycarbonyl-4-(2,3-dichlorophenyl)-pyridine-5-carboxy]hexyl]-isothiuronium iodide and 0.35 g (2.8 mmol) of 3-(1H-imidazol-4-yl)propylamine. 0.63 g (30%) of a pale yellow, amorphous solid.

$C_{29}H_{39}Cl_2IN_6O_4$ (733.48). Rf ($CH_3COOC_2H_5/CH_3OH/NH_4Cl/NH_3$ buffer 60:38:2): 0.42.

| $^1$H—NMR data: (CD$_3$OD, TMS as internal standard) | $\delta =$ | 1.1–1.8 (m) | 8H |
|---|---|---|---|
| | | 1.8–2.1 (quin) | 3H |
| | | 2.3 (s) | 3H |
| | | 2.35 (s) | 3H |
| | | 2.7 (t) | 2H |
| | | 3.1–3.4 (m) | 4H |
| | | 3.6 (s) | 3H |
| | | 3.9–4.2 (m) | 2H |
| | | 4.9 (broad) | 6H, replaceable by D$_2$O |
| | | 5.5 (s) | 1H |
| | | 6.95 (s) | 1H |
| | | 7.1–7.5 (m) | 3H |
| | | 7.75 (s) | 1H ppm. |

EXAMPLE 20

$N^1$-[6-[1,4-Dihydro-2,6-dimethyl-3-isobutoxycarbonyl-4-(3-nitrophenyl)-pyridine-5-carboxy]hexyl]-$N^2$-[3-(1H-imidazol-4-yl)propyl]-guanidine hydriodide

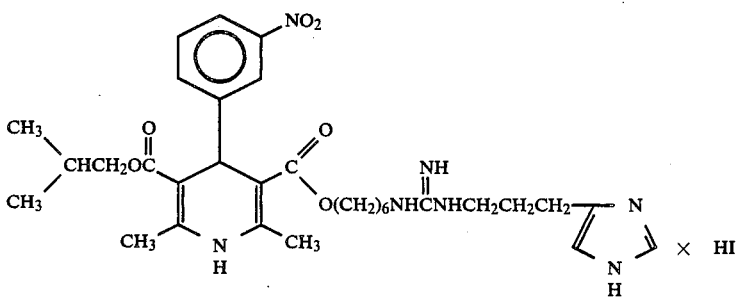

(a)
1,4-Dihydro-2,6-dimethyl-3-isobutoxycarbonyl-4-(3-nitrophenyl)-5-(6-phthalimido-hexyloxy)carbonyl-pyridine Prepared by a method analogous to that of Example 1(a) from 7.0 g (24 mmol) of 2-(3-nitrobenzylidene)-acetoacetic acid isobutylester and 8.0 g (24 mmol) of 3-amino-crotonic acid-(6-phthalimidohexyl)ester. 14.6 g (quantitative) of an orange yellow oil which is used for further reactions without purification.

$C_{33}H_{37}N_3O_8$ (603.67). Rf ($CH_2Cl_2/CH_3OH$ 98:2): 0.34.

(b)
1,4-Dihydro-2,6-dimethyl-3-isobutoxycarbonyl-4-(3-nitrophenyl)-5-(6-aminohexyloxy)carbonyl-pyridine Prepared by a method analogous to that of Example 1(b) from 13.28 g (22 mmol) of 1,4-dihydro-2,6-dimethyl-3-isobutoxycarbonyl-4-(3-nitrophenyl)-5-(6-phthalimidohexyloxy)carbonyl-pyridine and 3.3 ml (66 mmol) of hydrazine hydrate. 9.02 g (86%) of a yellow oil.

$C_{25}H_{35}N_3O_6$ (473.57). Rf ($CH_2Cl_2/CH_3OH$ 80:20): 0.16.

(c)
$N^1$-Benzoyl-$N^2$-[6-[1,4-dihydro-2,6-dimethyl-3-isobutoxycarbonyl-4-(3-nitrophenyl)-pyridine-5-carboxy]hexyl]-thiourea Prepared by a method analogous to that of Example 1(c) from 9.0 g (19 mmol) of 1,4-dihydro-2,6-dimethyl-3-isobutoxycarbonyl-4-(3-nitrophenyl)-5-(6-aminohexyloxy)carbonyl-pyridine and 3.1 g (19 mmol) of benzoylisothiocyanate. 5.7 g (47%) of a yellow, amorphous solid obtained after chromatographic purification on silica gel with dichloromethane/methanol (98:2) as solvent.

$C_{33}H_{40}N_4O_7S$ (636.77). Rf ($CH_2Cl_2/CH_3OH$ 95:5): 0.76.

(d)
S-Methyl-N-[6-[1,4-dihydro-2,6-dimethyl-3-isobutoxycarbonyl-4-(3-nitrophenyl)-pyridine-5-carboxy]hexyl]-isothiuronium iodide Prepared by a method analogous to that of Example 1(d) from 3.0 g (4.7 mmol) of $N^1$-benzoyl-$N^2$-[6-[1,4-dihydro-2,6-dimethyl-3-isobutoxycarbonyl-4-(3-nitrophenyl)-pyridine-5-carboxy]hexyl]-thiourea. 2.6 g (81%) of a yellow, amorphous solid.

$C_{27}H_{29}IN_4O_6S$ (674.60). Rf ($CH_2Cl_2/CH_3OH$ 80:20): 0.66.

(e)
$N^1$-[6-[1,4-Dihydro-2,6-dimethyl-3-isobutoxycarbonyl-4-(3-nitrophenyl)-pyridine-5-carboxy]hexyl]-$N^2$-[3-(1H-imidazol-4-yl)propyl]-guanidine hydriodide Prepared by a method analogous to that of Example 1(e) from 1.50 g (2.2 mmol) of S-methyl-N-[6-[1,4-dihydro-2,6-dimethyl-3-isobutoxycarbonyl-4-(3-nitrophenyl)-pyridine-5-carboxy]hexyl]-isothiuronium iodide and 0.28 g (2.2 mmol) of 3-(1H-imidazol-4- yl)propylamine. 0.71 g (42%) of a pale yellow, amorphous solid.

$C_{32}H_{46}IN_7O_6$ (751.66). Rf ($CH_3COOC_2H_5$/$CH_3OH$/$NH_4Cl$/$NH_3$ buffer 50:47.5:2.5): 0.64.

| $^1$H—NMR data: (CD$_3$OD, TMS as internal standard) | δ = 0.8–1.0 (2d) | 6H |
|---|---|---|
| | 1.2–2.1 (m) | 3H |
| | 2.4 (s) | 6H |
| | 2.7 (t) | 2H |
| | 3.1–3.4 (m) | 4H |
| | 3.85 (d) | 2H |
| | 4.1 (t) | 2H |
| | 4.8 (broad) | 6H, replaceable by D$_2$O |
| | 5.2 (s) | 1H |
| | 6.95 (s) | 1H |
| | 7.4–8.3 (m) | 5H ppm. |

Example 21

N$^1$-[8-[1,4-Dihydro-2,6-dimethyl-3-methoxycarbonyl-4-(3-nitrophenyl)-pyridine-5-carboxy]octyl]-N$^2$-[3-(1H-imidazol-4-yl)propyl]-guanidine hydriodide

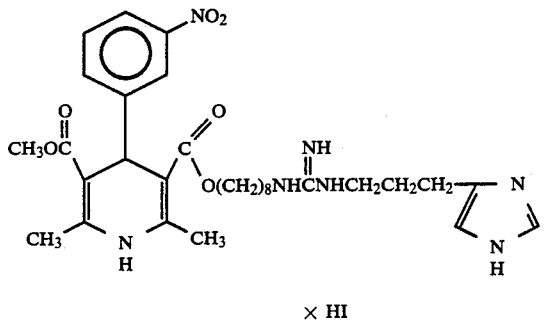

(a) 1,4-Dihydro-2,6-dimethyl-3-methoxycarbonyl-4-(3-nitrophenyl)-5-(8-phthalimido-octyloxy)carbonyl-pyridine 6.68 g (13.6 mmol) of 2-(3-nitrobenzylidene)-acetoacetic acid-(8-phthalimidooctyl)ester and 1.57 g (13.6 mmol) of 3-amino-crotonic acid methyl ester are boiled under reflux in 70 ml of isopropanol for 5 hours. The oil obtained after removal of the solvent by evaporation under vacuum is chromatographed on silica gel with dichloromethane/methanol (97:3) as solvent. 6.75 g (85%) of a yellow oil are obtained.

$C_{32}H_{35}N_3O_8$ (589.64). Rf ($CH_2Cl_2$/$CH_3OH$ 95:5): 0.5.

(b) 1,4-Dihydro-2,6-dimethyl-3-methoxycarbonyl-4-(3-nitrophenyl)-5-(8-aminooctyloxy)carbonyl-pyridine Prepared by a method analogous to that of Example 1(b) from 6.75 g (11.5 mmol) of 1,4-dihydro-2,6-dimethyl-3-methoxycarbonyl-4-(3-nitrophenyl)-5-(8-phthalimidooctyloxy)carbonyl-pyridine and 1.7 ml (34.5 mmol) of hydrazine hydrate. 4.13 g (78%) of yellow crystals melting at 129°–131° C. obtained with tert.-butyl methyl ether.

$C_{24}H_{33}N_3O_6$ (459.54). Rf ($CH_2Cl_2$/$CH_3OH$ 70:30): 0.15.

(c) N$^1$-Benzoyl-N$^2$-[8-[1,4-dihydro-2,6-dimethyl-3-methoxycarbonyl-4-(3-nitrophenyl)-pyridine-5-carboxy]octyl]-thiourea Prepared by a method analogous to that of Example 1(c) from 3.1 g (6.8 mmol) of 1,4-dihydro-2,6-dimethyl-3-methoxycarbonyl-4-(3-nitrophenyl)-5-(8-aminooctyloxy)carbonyl-pyridine and 1.1 g (6.8 mmol) of benzoylisothiocyanate. Chromatographic purification on silica gel with dichloromethane/methanol (99:1) as solvent yields 3.7 g (87%) of a yellow oil.

$C_{32}H_{38}N_4O_7S$ (622.74). Rf ($CH_2Cl_2$/$CH_3OH$ 98:2): 0.3.

(d) S-Methyl-N-[8-[1,4-dihydro-2,6-dimethyl-3-methoxycarbonyl-4-(3-nitrophenyl)-pyridine-5-carboxy]octyl]-isothiuronium iodide Prepared by a method analogous to that of Example 1(d) from 3.7 g (5.9 mmol) of N$^1$-benzoyl-N$^2$-[8-[1,4-dihydro-2,6-dimethyl-3-methoxycarbonyl-4-(3-nitrophenyl)-pyridine-5-carboxy]octyl]thiourea. 3.5 g (90%) of a yellow, amorphous solid.

$C_{26}H_{37}IN_4O_6S$ (660.53). Rf ($CH_2Cl_2$/$CH_3OH$ 9:1): 0.4.

(e) N$^1$-[8-[1,4-dihydro-2,6-dimethyl-3-methoxycarbonyl-4-(3-nitrophenyl)-pyridine-5-carboxy]-octyl]-N$^2$-[3-(1H-imidazol-4-ylpropyl]-guanidine hydriodide Prepared by a method analogous to that of Example 1(e) from 1.20 g (1.82 mmol) of S-methyl-N-[8-[1,4-dihydro-2,6-dimethyl-3-methoxycarbonyl-4-(3-nitrophenyl)-pyridine-5-carboxy]octyl]-isothiuronium iodide and 0.23 g (1.82 mmol) of 3-(1H-imidazol-4-yl)-propylamine. 0.45 g (33%) of a yellow, amorphous solid.

$C_{31}H_{44}IN_7O_6$ (737.64). Rf ($CH_3COOC_2H_5$/$CH_3OH$/$NH_4Cl$/$NH_3$ buffer 50:47.5:2.5): 0.6.

| $^1$H—NMR data: (CD$_3$OD, TMS as internal standard) | δ = 1.2–2.1 (m) | 14H |
|---|---|---|
| | 2.35 (s) | 3H |
| | 2.4 (s) | 3H |
| | 2.7 (t) | 2H |
| | 3.1–3.4 (m) | 4H |
| | 3.7 (s) | 3H |
| | 3.9–4.3 (m) | 2H |
| | 4.9 (broad) | 6H, replaceable by D$_2$O |
| | 5.15 (s) | 1H |
| | 6.95 (s) | 1H |
| | 7.4–8.2 (m) | 5H ppm. |

Example 22

$N^1$-[11-[1,4-Dihydro-2,6-dimethyl-3-methoxycarbonyl-4-(3-nitrophenyl)-pyridine-5-carboxy]undecyl]-$N^2$-[3-(1H-imidazol-4-yl)propyl]-guanidine hydriodide

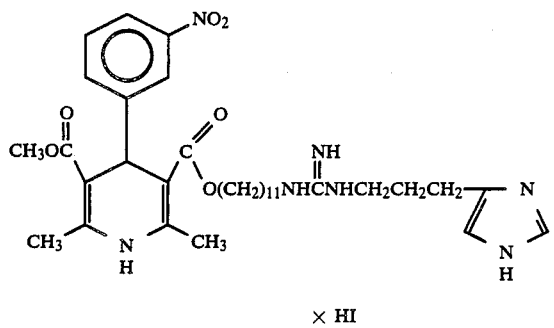

(a)
1,4-Dihydro-2,6-dimethyl-3-methoxycarbonyl-4-(3-nitrophenyl)-5-(11-phthalimido-undecyloxy)carbonyl-pyridine Prepared by a method analogous to that of Example 1(a) from 9.33 g (37.5 mmol) of 2-(3-nitrobenzylidene)-acetoacetic acid methyl ester and 15.00 g (37.5 mmol) of 3-amino-crotonic acid-(11-phthalimido-undecyl)ester. 23.18 g (98%) of yellow crystals, melting point 130°–132° C., obtained from methanol.

$C_{35}H_{41}N_3O_8$ (631.73). Rf ($CH_2Cl_2/CH_3OH$ 95:5): 0.78.

(b)
1,4-Dihydro-2,6-dimethyl-3-methoxycarbonyl-4-(3-nitrophenyl)-5-(11-aminoundecyloxy)carbonyl-pyridine Prepared by a method analogous to that of Example 1(b) from 18.95 g (30 mmol) of 1,4-dihydro-2,6-dimethyl-3-methoxycarbonyl-4-(3-nitrophenyl)-5-(11-phthalimido-undecyloxy)carbonyl-pyridine and 4.5 ml (90 mmol) of hydrazine hydrate. 15.0 g of a yellow oil which is used for further reactions without purification.

$C_{27}H_{39}N_3O_6$ (501.62). Rf ($CH_3OH/NH_3$ conc. 95:5): 0.59.

(c)
$N^1$Benzoyl-$N^2$-[11-[1,4-Dihydro-2,6-dimethyl-3-methoxycarbonyl-4-(3-nitrophenyl)-pyridine-5-carboxy]-undecyl]thiourea Prepared by a method analogous to that of Example 1(c) from 10.03 g (20 mmol) of 1,4-dihydro-2,6-dimethyl-3-methoxycarbonyl-4-(3-nitrophenyl)-5-(11-aminoundecyloxy)carbonyl-pyridine and 3.26 g (20 mmol) of benzoyl isothiocyanate. 5.20 g (39%) of a viscous, yellow oil obtained after chromatographic purification on silica gel with dichloromethane/methanol (98:2) as solvent.

$C_{35}H_{44}N_4O_7S$ (664.82). Rf ($CH_2Cl_2/CH_3OH$ 98:2): 0.55.

(d)
S-Methyl-N-[11-[1,4-dihydro-2,6-dimethyl-3-methoxycarbonyl-4-(3-nitrophenyl)-pyridine-5-carboxy]undecyl]-isothiuronium iodide Prepared by a method analogous to that of Example 1(d) from 4.0 g (6 mmol) of $N^1$-benzoyl-$N^2$-[11-[1,4-dihydro-2,6-dimethyl-3-methoxycarbonyl-4-(3-nitrophenyl)-pyridine-5-carboxy]undecyl]-thiourea. 3.8 g (90%) of a yellow, amorphous solid.

$C_{29}H_{43}IN_4O_6S$ (702.65). Rf ($CH_2Cl_2/CH_3OH$ 9:1): 0.43.

(e)
$N^1$-[11-[1,4-Dihydro-2,6-dimethyl-3-methoxycarbonyl-4-(3-nitrophenyl)-pyridine-5-carboxy]undecyl]-$N^2$-[3-(1H-imidazol-4-yl)propyl]-guanidine hydriodide Prepared by a method analogous to that of Example 1(e) from 1.50 g (2.13 mmol) of S-methyl-N-[11-[1,4-dihydro-2,6-dimethyl-3-methoxycarbonyl-4-(3-nitrophenyl)-pyridine-5-carboxy]undecyl]-isothiuronium iodide and 0.27 g (2.13 mmol) of 3-(1H-imidazol-4-yl)propylamine. 0.55 (33%) of a yellow, amorphous solid.

$C_{34}H_{50}IN_7O_6$ (779.72). Rf ($CH_3COOC_2H_5/CH_3OH/NH_4Cl/NH_3$ buffer 60:38:2): 0.33.

| $^1$H—NMR data: (CD$_3$OD, TMS as internal standard) | δ = 1.2–2.1 (m) | 20H |
|---|---|---|
| | 2.35 (s) | 3H |
| | 2.4 (s) | 3H |
| | 2.7 (t) | 2H |
| | 3.1–3.4 (m) | 4H |
| | 3.7 (s) | 3H |
| | 3.9–4.2 (m) | 2H |
| | 4.9 (broad) | 6H, replaceable by D$_2$O |
| | 5.15 (s) | 1H |
| | 6.95 (s) | 1H |
| | 7.4–8.3 (m) | 5H ppm. |

Example 23

$N^1$[2-[1,4-Dihydro-2,6-dimethyl-3-methoxycarbonyl-4-(benzofurazan-4-yl)-pyridine-5-carboxy]ethyl]-$N^2$-[3-(1H-imidazol-4-yl)propyl]-guanidine hydriodide

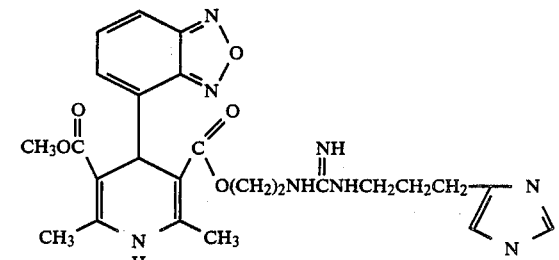

(a)
1,4-Dihydro-2,6-dimethyl-3-methoxycarbonyl-4-(benzofurazan-4-yl)-5-(phthalimido-ethoxy)carbonyl-pyridine 6.3 g (15.5 mmol) of 2-(benzofurazan-4-yl)-acetoacetic acid-(2-phthalimidoethyl)ester and 1.8 g (15.5 mmol) of 3-amino-crotonic acid methyl ester are boiled in 50 ml of isopropanol for 2 hours. The precipitate obtained on cooling to room temperature is suction filtered and recrystallised from ethanol. 5.0 g (64%) of yellow crystals melting at 208°–209° C.

$C_{26}H_{22}N_4O_7$ (502.48). Rf ($CH_2Cl_2/CH_3OH$ 95:5): 0.7.

(b)
1,4-Dihydro-2,6-dimethyl-3-methoxycarbonyl-4-(benzofurazan-4-yl)-5-(2-aminoethoxy)carbonyl-pyridine Prepared by a method analogous to that of Example 1(b) from 5.0 g (10 mmol) of 1,4-dihydro-2,6-dimethyl-3-methoxycarbonyl-4-(benzofurazan-4-yl)-5-(2-phthalimido-ethoxy)-carbonyl-pyridine and 1.5 ml (30 mmol) of hydrazine hydrate. 3.7 g (quantitative) of an orange yellow oil which is used for further reactions without purification.

$C_{18}H_{20}N_4O_5$ (372.38). Rf ($CH_2Cl_2/CH_3OH$ 80:20): 0.35.

(c)
$N^1$-Benzoyl-$N^2$-[2-[1,4-dihydro-2,6-dimethyl-3-methoxycarbonyl-4-(benzofurazan-4-yl)-pyridine-5-carboxy]ethyl]-thiourea Prepared by a method analogous to that of Example 1(c) from 2.9 g (7.8 mmol) of 1,4-dihydro-2,6-dimethyl-3-methoxycarbonyl-4-(benzofurazan-4-yl)-5-(2-aminoethoxy)carbonyl-pyridine and 1.3 g (7.8 mmol) of benzoylisothiocyanate. 2.4 g (58%) of a yellow, amorphous solid obtained after chromatography on silica gel using dichloromethane/methanol (99:1) as solvent.

$C_{26}H_{25}N_5O_6S$ (535.58). Rf ($CH_2Cl_2/CH_3OH$ (99:1): 0.4.

(d)
S-Methyl-N-[2-[1,4-dihydro-2,6-dimethyl-3-methoxycarbonyl-4-(benzofurazan-4-yl)-pyridine-5-carboxy]ethyl]-isothiuronium iodide Prepared by a method analogous to that of Example 1(d) from 2.24 g (4.2 mmol) of $N^1$-benzoyl-$N^2$-[2-[1,4-dihydro-2,6-dimethyl-3-methoxycarbonyl-4-(benzofurazan-4-yl)-pyridine-5-carboxy]ethyl]-thiourea. 2.20 g (91%) of a yellow, amorphous solid.

$C_{20}H_{24}IN_5O_5S$ (573.41). Rf ($CH_2Cl_2/CH_3OH$ 9:1): 0.4.

(e)
$N^1$-[2-[1,4-Dihydro-2,6-dimethyl-3-methoxycarbonyl-4-(benzofurazan-4-yl)-pyridine-5-carboxy]ethyl]-$N^2$-[3-(1H-imidazol-4-yl)propyl]-guanidine hydriodide Prepared by a method analogous to that of Example 1(e) from 1.2 g (2.1 mmol) of S-methyl-N-[2-[1,4-dihydro-2,6-dimethyl-3-methoxycarbonyl-4-(benzofurazan-4-yl)-pyridine-5-carboxy]ethyl]-isothiuronium iodide and 0.26 g (2.1 mmol) of 3-(1H-imidazol-4-yl) propylamine. 0.35 g (26%) of a pale yellow, amorphous solid.

$C_{25}H_{31}IN_8O_5$ (650.48). Rf ($CH_3COOC_2H_5$/$CH_3OH$/$NH_4Cl$/$NH_3$ buffer 50:47.5:2.5): 0.65.

| $^1$H—NMR data: (CD$_3$OD, TMS as internal standard) | δ = 1.8–2.2 (m) | 2H |
|---|---|---|
| | 2.4 (s) | 6H |
| | 2.7 (t) | 2H |
| | 3.2–3.7 (m) | 4H |
| | 3.65 (s) | 3H |
| | 4.0–4.5 (m) | 2H |
| | 4.9 (broad) | 6H, replaceable by D$_2$O |
| | 5.65 (s) | 1H |
| | 6.95 (s) | 1H |
| | 7.3–7.9 (m) | 4H ppm. |

Example 24
8-[1,4-Dihydro-2,6-dimethyl-3-methoxycarbonyl-4-(3-nitrophenyl)-pyridine-5-carboxy]-N-[3-(1H-imidazol-4-yl)propyl]caprylamidine hydrochloride

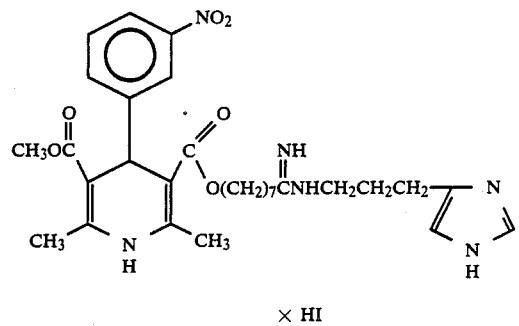

× HI (a)
1,4-Dihydro-2,6-dimethyl-3-methoxycarbonyl-4-(3-nitrophenyl)-5-(7-cyanoheptyloxy)carbonyl-pyridine 6.7 g (26.8 mmol) of 2-(3-nitrobenzylidene)-acetoacetic acid methyl ester and 6.0 g (26.8 mmol) of 3-amino-crotonic acid-(7-cyanoheptyl)ester are boiled in 50 ml of isopropanol for 12 hours. The precipitate which separates is suction filtered and chromatographed on silica gel with dichloromethane/methanol (98:2). The main fraction yields 7.9 g (65%) of yellow crystals melting at 151°–152° C. after concentration of the fraction by evaporation under vacuum and recrystallisation of the residue from tert.-butyl-methyl ether.

$C_{24}H_{29}N_3O_6$ (455.51). Rf ($CH_2Cl_2/CH_3OH$ 98:2): 0.4.

(b)
8-[1,4-Dihydro-2,6-dimethyl-3-methoxycarbonyl-4-(3-nitrophenyl)-pyridine-5-carboxy]-caprylimidic acid methyl ester dihydrochloride Prepared by a method analogous to that of Example 12(b) from 2.0 g (4.4 mmol) of 1,4-dihydro-2,6-dimethyl-3-methoxycarbonyl-4-(3-nitrophenyl)-5-(7-cyanoheptyloxy)carbonyl-pyridine. 2.5 g of a yellow, hygroscopic foam.

$C_{25}H_{35}Cl_2N_3O_7$ (560.47). Rf ($CH_2Cl_2/CH_3OH/N(C_2H_5)_3$ 90:10:1): 0.6.

(c)
8-[1,4-Dihydro-2,6-dimethyl-3-methoxycarbonyl-4-(3-nitrophenyl)-pyridine-5-carboxy]-N-3-(1H-imidazol-4yl)propyl]-caprylamidine hydrochloride Prepared by a method analogous to that of Example 12(c) from 1.50 g (2.7 mmol) of 8-[1,4-dihydro-2,6-dimethyl-3-methoxycarbonyl-4-(3-nitrophenyl)-pyridine-5-carboxy]-caprylimidic acid-methyl ester hydrochloride and 0.38 g (3.0 mmol) of 3-(1H-imidazol-4-yl)propylamine. 0.63 g (38%) of a pale yellow, amorphous solid.

$C_{30}H_{41}ClN_6O_6$ (617.15). Rf ($CH_3COOC_2H_5$/$CH_3OH$/$NH_4Cl$/$NH_3$ buffer 50:47.5:2.5): 0.65.

| $^1$H—NMR data: (CD$_3$OD, TMS as internal standard) | δ = 1.1–2.2 (m) | 12H |
|---|---|---|
| | 2.35 (s) | 3H |
| | 2.4 (s) | 3H |
| | 2.4–2.9 (m) | 4H |
| | 3.2–3.5 (t) | 2H |
| | 3.7 (s) | 3H |

| -continued | |
|---|---|
| 3.9–4.2 (m) | 2H |
| 5.0 (broad) | 5H, replaceable by D₂O, |
| 5.15 (s) | 1H |
| 6.95 (s) | 1H |
| 7.4–8.3 (m) | 5H, ppm. |

We claim:

1. A 1,4-dihydropyridine compound of the following formula I

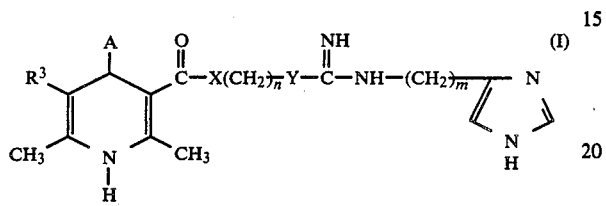

wherein A is

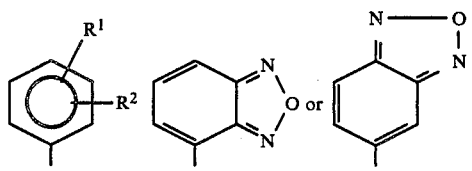

wherein

R¹ and R², which may be identical or different, are each a hydrogen atom, a straight or branched chain, $C_1$–$C_4$ alkyl radical, a substituted such radical bearing at least one halogen atom, $C_1$ to $C_4$ alkoxy group or phenyl group, a halogen atom, a nitro group or a trifluoromethyl group;

R³ is a nitro group or the group

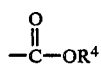

wherein R⁴ is a straight or branch chain $C_1$–$C_4$ alkyl radical or a substituted such radical bearing at least one halogen or $C_1$–$C_4$ alkoxy group;

X is an oxygen atom or NH group;

Y is an NH group or a valence bond;

n is an integer from 1 to 16; and m is 2 or 3;

or a physiologically acceptable salt thereof.

2. A 1,4-dihydropyridine compound according to claim 1, wherein R¹ and R² are each attached in one of the 2 or 3 positions of the phenyl ring.

3. A 1,4-dihydropyridine compound according to claim 1, wherein A is

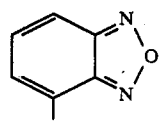

4. A 1,4-dihydropyridine compound according to claim 1, wherein R¹ and R² are identical or different and are each a hydrogen atom, a chlorine atom or a nitro group and wherein R¹ and R² are each attached to one of the 2 or 3 positions of the phenyl ring;

R³ is

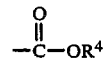

wherein R⁴ is a straight or branch chain $C_1$–$C_4$ alkyl radical or a substituted such radical bearing at least one halogen or $C_1$–$C_4$ alkoxy group; and n is an integer from 2 to 6.

5. A 1,4-dihydropyridine derivative according to claim 1, wherein R¹ is a hydrogen atom and R² is a nitro group, X is an oxygen atom;

Y is an NH group, and m is 3.

6. A medicament for treatment of cardiac disease, hypertension and arterial occlusion, comprising an effective amount of a compound according to claims 1, 2, 3, 4, or 5, together with an inert, pharmaceutically acceptable carrier or diluent.

* * * * *